(12) United States Patent
Berd

(10) Patent No.: US 7,560,103 B2
(45) Date of Patent: *Jul. 14, 2009

(54) COMPOSITION AND METHOD OF USING CARCINOMA TUMOR CELLS

(75) Inventor: David Berd, Wyncote, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/025,195

(22) Filed: Dec. 19, 2001

(65) Prior Publication Data

US 2003/0064080 A1    Apr. 3, 2003

Related U.S. Application Data

(60) Division of application No. 09/134,465, filed on Aug. 14, 1998, now Pat. No. 6,333,028, which is a continuation-in-part of application No. 08/899,905, filed on Jul. 24, 1997, now abandoned.

(51) Int. Cl.
   *A61K 45/00* (2006.01)
(52) U.S. Cl. ............... 424/93.7; 424/277.1; 424/184.1; 424/193.1; 424/278.1; 424/520
(58) Field of Classification Search ............... 424/93.1, 424/193.1, 194.1, 278.1, 93.7, 184.1, 277.1, 424/520, 573
See application file for complete search history.

(56) References Cited

U.S. PATENT DOCUMENTS

| 5,290,551 | A | * | 3/1994 | Berd | 424/193.1 |
| 5,484,596 | A |   | 1/1996 | Hanna, Jr. et al. | 424/277.1 |
| 5,637,483 | A |   | 6/1997 | Dranoff et al. | 424/93.21 |
| 6,333,028 | B1 | * | 12/2001 | Berd |  |
| 6,458,369 | B1 | * | 10/2002 | Berd | 424/277.1 |

FOREIGN PATENT DOCUMENTS

| WO | WO 96/40173 | 12/1996 |
| WO | WO 9640173 A1 * | 12/1996 |

OTHER PUBLICATIONS

Hoover et al( Cancer, 1985, 55:1236-1243).*
Livingston et al (Can. Res., 1989,49:7045-7050).*
Webster's II New Rivewrside University Dictionary, 1994, Houghton Mifflin Co., Boston, MA, p. 1155.*
Sensi et al. (J. Clin. Invest. 1997; 99: 710-717).*
Hoover et al. (Cancer, 1985: 55: 1236-1243).*
Marx, Jean L., Cancer Vaccines Show Promise at Last, Science, 245:813-815, 1989.
Hellström and Hellström, Tumor Immunology: An Overview, ANAYS, 690:24-33, 1993.
Dillman et al., "Irradiated, Cultured, Autologous Tumor Cells for Active Specific Immunotherapy", Proceedings of ASCO 14:546 (#1810), 1995.
Advani, S. et al., Oncology,42:275-281, 1985.
Berd, D. et al., Proc. Ame. Assoc. Cancer Res., 36:677-678, 1995.
Berd et al., Proc. Am Soc. Clin Oncol. 2:56, Abstract C-217.
Dunton, C.J., et al. Gynecologic Oncology, 68:111, 1998.
Fugiwara, H. et al., J. Immunol., 132:1571-1577, 1984.
D. Berd et al., "Induction of Delayed-Type Hypersensitivity (DTH) to Ovarian Cancer Cells After Treatment With An Autologous (AUT), Hapten-Modified Vaccine," *Proceedings of the American Association for Cancer Research Annual*, vol. 39, Mar. 1998, p. 356.
G. Garcia Manero et al., "Immunotherapy With an Autologous Cell Vaccine In Patients With Acute Myelogenous Leukemia (AML) in Second Remission," *Blood*, vol. 98, No. 11, Nov. 2001, p. 212b.
Mastrangelo, M. J. et al., Melanoma Research, 5:443, 1995.
Nahas, F. et. al., Cell. Immunol., 54:241-247, 1980.
Sato, T., Cancer Immunol. Immunother., 43:174-179, 1996.
Benjamin et al., Recent Results in Cancer Research 47:408-414, 1974.
Wiseman et al., Western J. Med. 151:283-288, 1989.
MacLean et al., J. Immunotherapy 11:292-305, 1992.
Longnecker, B.M., Soc. Biol. Therapy Annual Meeting, p. 31, 1992.
Levin et al., (in Human Tumours In Short Term Culture: Techniques and Clinical Applications, P.P.. Dendy, ed., Academic Press, London, pp. 277-280), 1976.
Gillette et al. J. Reticulo Soc., 30:331-339, 1981.
Sherman et al. J. Immunol., 123:501-502, 1979.
Bystryn, Cancer Metastasis Rev., 9:81-90, 1990.
Robins, Pathologic Basis of Disease, Fifth Edition, 1994, p. 1065.
PR Newswire (May 22, 2000) 1023, AVAX Technologies' O-Vac(TM) cancer Vaccine Induces Positive Immunological and Clinical Outcomes in Patients with Advanced Ovarian Cancer.
A. Bodurtha et al., "A clinical, histologic, and immunologic study of a case of metastatic malignant melanoma undergoing spontaneous remission." Cancer 37: 735-42, 1976.
D. Elder et al., "The surgical pathology of cutaneous malignant melanoma." Human Malignant Melanoma, edited by WH Clark et al. New York: Grune & Stratton; 1979, p. 55-108.
E. Creagan et al., "Recombinant leukocyte A interferon in the treatment of disseminated malignant melanoma." Cancer 58: 2576-1578, 1986.

(Continued)

*Primary Examiner*—Brandon J Fetterolf
(74) *Attorney, Agent, or Firm*—Morgan Lewis & Bockius, LLP

(57) ABSTRACT

The present invention is directed to compositions and methods of treating cancer. The compositions of the present invention include a composition prepared from a tumor cell which is hapten modified and syngeneic to the type of tumor to be treated. The composition has the properties, when administered with an adjuvant to a human suffering from a malignant tumor of the same type as said tumor cell, of eliciting T lymphocytes that infiltrate the tumor of said human, of eliciting an inflammatory immune response against the tumor of said human, and of eliciting a delayed-type hypersensitivity response to the tumor of said human. The methods of the present invention are directed to treating cancer comprising administering a therapeutically effective amount of a composition comprising a tumor cell.

3 Claims, 2 Drawing Sheets

OTHER PUBLICATIONS

T. Everson et al., "Spontaneous regression of cancer." Philadelphia: W.B. Saunders Company; 1966.

J. Harris et al., "Adjuvant active specific immunotherapy for stage II and III colon cancer with an autologous tumor cell vaccine." J Clin Oncol, vol. 18:1, 2000; pp. 148-157.

S. Rosenberg, "Progress in human tumour immunology and immunotherapy." Nature, May 17, 2001; vol. 411: 380-4.

J Vermorken et al., "Active specific immunotherapy for stage II and stage III human colon cancer: a randomised trial." Lancet 1999; 353: 345-50.

* cited by examiner

COMPOSITION AND METHOD OF USING CARCINOMA TUMOR CELLS

CROSS REFERENCE TO RELATED APPLICATIONS

This application is a divisional patent application of U.S. application Ser. No. 09/134,465, filed Aug 14, 1998, now issued as U.S. Pat. No. 6,333,028, which is a continuation-in-part of U.S. application Ser. No. 08/899,905, filed Jul 24, 1997, now abandoned, both of which are incorporated herein by reference.

REFERENCE TO GOVERNMENT GRANTS

The invention described herein was made in the course of work under a grant or award from an NIH Cancer Research grant, grant no. CA39248. The United States Government may have certain rights in this invention.

BACKGROUND OF THE INVENTION

It was theorized in the 1960's that tumor cells bear specific antigens (TSA) which are not present on normal cells and that the immune response to these antigens might enable an individual to reject a tumor. It was later suggested that the immune response to TSA could be increased by introducing new immunological determinants on cells. Mitchison, *Transplant. Proc.*, 1970, 2, 92. Such a "helper determinant", which can be a hapten, a protein, a viral coat antigen, a transplantation antigen, or a xenogenous cell antigen, could be introduced into a population of tumor cells. The cells would then be injected into an individual who would be expected to be tolerant to the growth of unmodified tumor cells. Clinically, the hope was that an immunologic reaction would occur against the helper determinants, as a consequence of which the reaction to the accompanying TSA is increased, and tumor cells which would otherwise be tolerated are destroyed. Mitchison, supra, also suggests several modes of action of the helper determinants including 1) that the unmodified cells are merely attenuated, in the sense that their growth rate is slowed down or their susceptibility to uimmunologic attack increased; 2) that helper determinants merely provide points of attack and so enable the modified cells to be killed by an immune response not directed against TSA; 3) that the helper determinants have an adjuvant action such as binding to an antibody or promoting localization of the cells in the right part of the body for immunization, in particular, in lymph nodes.

Fujiwara et al., *J. Immunol.*, 1984a, 132, 1571 showed that certain haptenized tumor cells, i.e., tumor cells conjugated with the hapten trinitrophenyl (TNP), could induce systemic immunity against unmodified tumor cells in a murine system, provided that the mice were first sensitized to the hapten in the absence of hapten-specific suppressor T cells. Spleen cells from the treated mice completely and specifically prevented the growth of tumors in untreated recipient animals. Flood et al., *J. Immunol.*, 1987, 138, 3573 showed that mice immunized with a TNP-conjugated, ultraviolet light-induced "regressor" tumor were able to reject a TNP-conjugated "progressor" tumor that was otherwise non-immunologic. Moreover, these mice were subsequently resistant to challenge with unconjugated "progressor" tumor. In another experimental system, Fujiwara et al., *J. Immunol.*, 1984b, 133, 510 demonstrated that mice sensitized to trinitrochlorobenzene (TNCB) after cyclophosphamide pretreatment could be cured of large (10 mm) tumors by in situ haptenization of tumor cells; subsequently, these animals were specifically resistant to challenge with unconjugated tumor cells.

The teachings of Fujiwara et al. differ from the present invention for several reasons including the following: A. The cells used in Fujiwara's composition were derived from induced transplantable murine tumors—not from spontaneous human tumors; B. Fujiwara's composition is used in immunoprophylaxis—the present invention uses immunotherapy; C. Fujiwara's composition is administered as a local therapy—the present invention is administered by systemic inoculation; and D. Fujiwara's composition did not result in tumor regression—the composition of the present invention results in regression and/or prolonged survival for at least a substantial portion of the patients treated.

The existence of T cells which cross-react with unmodified tissues has recently been demonstrated. Weltzien and coworkers have shown that class I MHC-restricted T cell clones generated from mice immunized with TNP-modified syngeneic lymphocytes respond to MHC-associated, TNP-modified "self" peptides. Ortmann, B., et al., *J. Immunol.*, 1992, 148, 1445. In addition, it has been established that immunization of mice with TNP-modified lymphocytes results in the development of splenic T cells that exhibit secondary proliferative and cytotoxic responses to TNP-modified cells in vitro. Shearer, G. M. *Eur. J. Immunol.*, 1974, 4, 527. The potential of lymphocytes elicited by immunization with DNP- or TNP-modified autologous cells to respond to unmodified autologous cells is of considerable interest because it may be relevant to two clinical problems: 1) drug-induced autoimmune disease, and 2) cancer immunotherapy. In regard to the former, it has been suggested that ingested drugs act as haptens, which combine with normal tissue protein forming immunogenic complexes that are recognized by T cells. Tsutsui, H., et al., *J. Immunol.*, 1992, 149, 706. Subsequently, autoimmune disease, e.g., systemic lupus erythematosus, can develop and continue even after withdrawal of absence of the offending drug. This would imply the eventual generation of T lymphocytes that cross-react with unmodified tissues.

The common denominator of these experiments is sensitization with hapten in a milieu in which suppressor cells are not induced. Spleen cells from cyclophosphamide pretreated, TNCB-sensitized mice exhibited radioresistant "amplified helper function" i.e., they specifically augmented the in vitro generation of anti-TNP cytotoxicity. Moreover, once these amplified helpers had been activated by in vitro exposure to TNP-conjugated autologous lymphocytes, they were able to augment cytotoxicity to unrelated antigens as well, including tumor antigens (Fujiwara et al., 1984b). Flood et al., (1987), supra, showed that this amplified helper activity was mediated by T cells with the phenotype $Lyt^-1^+$, $Lyt^-2^-$, $L3T4^+$, $I^-J^+$ and suggests that these cells were contrasuppressor cells, a new class of immunoregulatory T cell.

Immunotherapy of patients with melanoma had shown that administration of cyclophosphamide, at high dose (1000 $mg/M^2$) or low dose (300 $mg/M^2$), three days before sensitization with the primary antigen keyhole limpet hemocyanin markedly augments the acquisition of delayed type hypersensitivity to that antigen (Berd et al., *Cancer Res.*, 1982, 42, 4862; *Cancer Res.*, 1984a, 44, 1275). Low dose cyclophosphamide pretreatment allows patients with metastatic melanoma to develop delayed type hypersensitivity to autologous melanoma cells in response to injection with autologous melanoma vaccine (Berd et al., *Cancer Res.*, 1986, 46, 2572). The combination of low dose cyclophosphamide and vaccine can produce clinically important regression of metastatic tumor (Berd et al. (1986), supra; *Cancer Invest.*, 1988a, 6, 335). Cyclophosphamide administration results in reduction of peripheral blood lymphocyte non-specific T suppressor function (Berd et al., *Cancer Res.*, 1984b, 44, 5439; *Cancer Res.*, 1987, 47, 3317), possibly by depleting CD4+, CD45R+ suppressor inducer T cells (Berd et al., *Cancer Res.*, 1988b, 48, 1671). The antitumor effects of this immunotherapy regimen appear to be limited by the excessively long interval between the initiation of vaccine administration and the development of delayed type hypersensitivity to the tumor cells (Berd et al., *Proc. Amer. Assoc. Cancer Res.*, 1988c, 29, 408 (#1626)). Therefore, there remained a need to increase the therapeutic efficiency of such a vaccine to make it more immunogenic.

Most tumor immunologists now agree that T lymphocytes, white cells responsible for tumor immunity, infiltration into the tumor mass is a prerequisite for tumor destruction by the immune system. Consequently, a good deal of attention has been focused on what has become known as "TIL" therapy, as pioneered by Dr. Stephen Rosenberg at NCL Dr. Rosenberg and others have extracted from human cancer metastases the few T lymphocytes that are naturally present and greatly expanded their numbers by culturing them in vitro with Interleukin 2 (IL2), a growth factor for T lymphocytes. Topalian et al., *J. Clin. Oncol.*, 1988, 6, 839. However this therapy has not been very effective because the injected T cells are limited in their ability to "home" to the tumor site.

The ability of high concentrations of IL2 to induce lymphocytes to become non-specifically cytotoxic killer cells has been exploited therapeutically in a number of studies (Lotze et al., *J. Biol. Response*, 1982, 3, 475; West et al., *New Engl. J. Med.*, 1987, 316, 898). However, this approach has been limited by the severe toxicity of high dose intravenous IL2. Less attention has been given to the observation that much lower concentrations of IL2 can act as an immunological adjuvant by inducing the expansion of antigen-activated T cells (Talmadge et al., *Cancer Res.*, 1987, 47, 5725; Meuer et al., *Lancet*, 1989, 1, 15). Therefore, there remains a need to understand and attempt to exploit the use of IL2 as an immunological adjuvant.

Human melanomas are believed to express unique surface antigens recognizable by T lymphocytes. Old, L. J., *Cancer Res.*, 1981, 41, 361; Van der Bruggen, P., et al., *Science*, 1991, 254, 1643; Mukhedi, B., et al., *J. Immunol.*, 1986, 136, 1888; and Anichini, A., et al., *J. Immunol.*, 1989, 142, 3692. However, immunotherapeutic approaches prior to work done by the present inventor had been limited by the difficulty of inducing an effective T cell-mediated response to such antigens in vivo.

The present inventor obtained results including substantial tumor remission and prolongation of survival time with a haptenized rumor cell vaccine administered to patients with malignant melanoma.

There are several models proposed to explain what appears to be tolerance to human tumor-associated antigens. They include:

1) Tumor antigen-specific suppressor cells that down-regulated incipient anti-tumor responses. Mukhedi, et al., supra; Berendt, M. J. and R. J. North., *J. Exp. Med.*, 1980, 151, 69.

2) Failure of human tumor cells to elicit T helper cells or to provide costimulatory signals to those T cells. Fearon, E. R., et al., *Cell*, 1990, 60, 397; Townsend, S. E. and J. P. Allison, *Science*, 1993, 259, 368; and 3) Reduced surface expression of major histocompatibility products on tumor cells which limits their recognition by T cells. Ruiter, D. J., *Seminars in Cancer Biology*, 1991, 2, 35. None of these hypotheses has yet been corroborated in a clinical system.

Regardless of whether such explanations are true or not, there is a continuing need for more effective treatment of various malignancies.

In regard to acute myelogenous leukemia (AML), the treatment for AML is divided into one or two initial induction phases and several courses of postremission, also known as consolidation, chemotherapy. Initial induction chemotherapy may induce a complete response in 55 to 88% of the patients, depending on the protocol used. However, the vast majority of these patients relapse, and the long-term (5 year+) survival of AML patients is only 20-30%. The addition of high-dose chemotherapy and bone marrow transplantation (BMT) to this therapeutic regime during the first remission can bring about modest improvements in result. For example, patients undergoing allogeneic BMT are afforded a 5 to 10% increase in the 5 year survival. However, the strict eligibility criteria for BMT (e.g., age, availability of an HLA-matched donor) severely limit the number of patients who can be treated. Once AML patients relapse, there is only a 30% chance of achieving a second remission, and very few of these patients remain disease-free in the long run. Treatment modalities on relapse include similar protocols to those used in achieving the first remission (induction therapy followed by several courses of consolidation chemotherapy), although high dose of a single agent and BMT can also be used (Keating et al.).

Experience with bone marrow transplantation has suggested that immunological rejection may play a role in the control of the disease. Graft-versus-host disease (GVHD) and relapse are the two main causes of death of patients treated with BMT. The risk of relapse decreases if mild GVHD occurs (Horowitz et al.). Therefore it has been hypothesized that grafted lymphocytes are able to immunologically reject host leukemia cells (graft-versus-leukemia reaction, GVL). This GVL reaction could be mediated by a T-cell response against specific leukemia cell antigens, although immunogenic human leukemia antigens have not yet been demonstrated (the same is true for melanoma). It is known that human AML cells strongly express both class I and class II major histocompatibility complex (MHC) antigens (Ashman et al.; Andreasen et al.) which are prerequisites for the induction of CD8- and CD4-mediated T cell responses, respectively. However, induction of a T cell response targeted to leukemia cells has not been successful.

Several immunological approaches have been used for the treatment of acute leukemia (Foon et al.; Caron and Scheinberg). These approaches are divided into non-specific, such as Bacillus Calmene Guerin (BCG), interleukin-2, levamisole, methanol-extraction residue of tubercle bacillus, and specific, such as monoclonal antibodies and vaccines (harvested leukemia cells, cell free extracts and cultured cells). The majority of these studies have been performed in patients already in remission, in which immunotherapy would have to be successful in controlling residual disease.

In the late 1960's and early 1970's the research group R. Powles at St. Barthlomew's Hospital in England conducted a series of studies of vaccine treatment of AML patients after chemotherapy-induced remission (Powles, 1974; Powles et al., 1977). They used allogeneic AML cells with BCG as an adjuvant. Several trials were performed, all with small sample sizes (N=10-15). There was some prolongation of survival with chemotherapy+immunotherapy compared with chemotherapy alone, but no prolongation of relapse-free survival. No serious toxicity was observed; autoimmunity (e.g., toxicity to normal bone marrow) was not seen. In retrospect, there were a number of technical problems with these trials: 1) allogeneic, rather than autologous, leukemia cells were used; 2) the dose of leukemia cells in the vaccine was excessive (up to $10^9$ cells/dose); 3) the BCG dose was very high and BCG administration was separated by time and location from the leukemia cell vaccine; and 4) the vaccine was administered while the patients were receiving cytotoxic drugs (maintenance or consolidation chemotherapy).

The immunochemical basis of this phenomenon remains speculative, but several hypotheses are being tested. Kim and Jang (1992) have suggested that the lack of T cell response to a particular epitope may not be due to absence of a T cell repertoire, but rather to difficulty in generating the particular epitope. Martin et al. (1993) have explained their results by hypothesizing the existence of autoreactive T cells that escape thymic selection because of low affinity for "self" peptides. Hapten modification of such peptides may convert subdominant peptide epitopes into dominant determinants and thereby activate those T cells. Alternatively, hapten modification may facilitate antigen processing to generate the epitope.

This therapeutic regime results in elicitation of 1) T lymphocytes to infiltrate the tumor, 2) an inflammatory immune response to a tumor, and 3) a delayed-type hypersensitivity response to the tumor, and, ultimately, in at least a portion of the patient population in tumor regression (reduction of tumor burden).

Conventional attempts to treat human cancer have been unsuccessful. Administration of compositions, exemplified by those set forth above, failed to reliably induce the development of cell-mediated immunity as indicated by delayed-type hypersensitivity (DTH), T cell infiltration, and inflammatory immune response.

Accordingly, despite the number of theories proposed for the immunological effects reported in the treatments of cancer, there remains a need for a composition which, upon administration to an animal, is capable of eliciting T lymphocytes that infiltrate a tumor, eliciting an inflammatory immune response to a tumor, and eliciting a delayed-type hypersensitivity response to a tumor.

SUMMARY OF THE INVENTION

The present invention is directed to a composition for treating adenocarcinoma, such as ovarian cancer and colon cancer, and various types of leukemia comprising a hapten modified syngeneic human tumor cell, wherein said tumor is selected from the group consisting of adenocarcinoma and leukemia, and said hapten modified tumor cell is substantially in a no growth phase. The composition has the property, when administered with an adjuvant to a human suffering from a malignant tumor of the same type as said tumor cell, of eliciting 1) T lymphocytes that infiltrate a tumor of the foregoing type, 2) an inflammatory immune response to the tumor, and 3) a delayed-type hypersensitivity response to the tumor.

The present invention so directed. to a method of administering a composition to treat malignancy of the foregoing types comprising administering to a person in need of such treatment a therapeutically effective amount of a hapten modified syngeneic human tumor cell substantially in a no growth phase and an adjuvant.

DETAILED DESCRIPTION OF THE INVENTION

Figure 1:
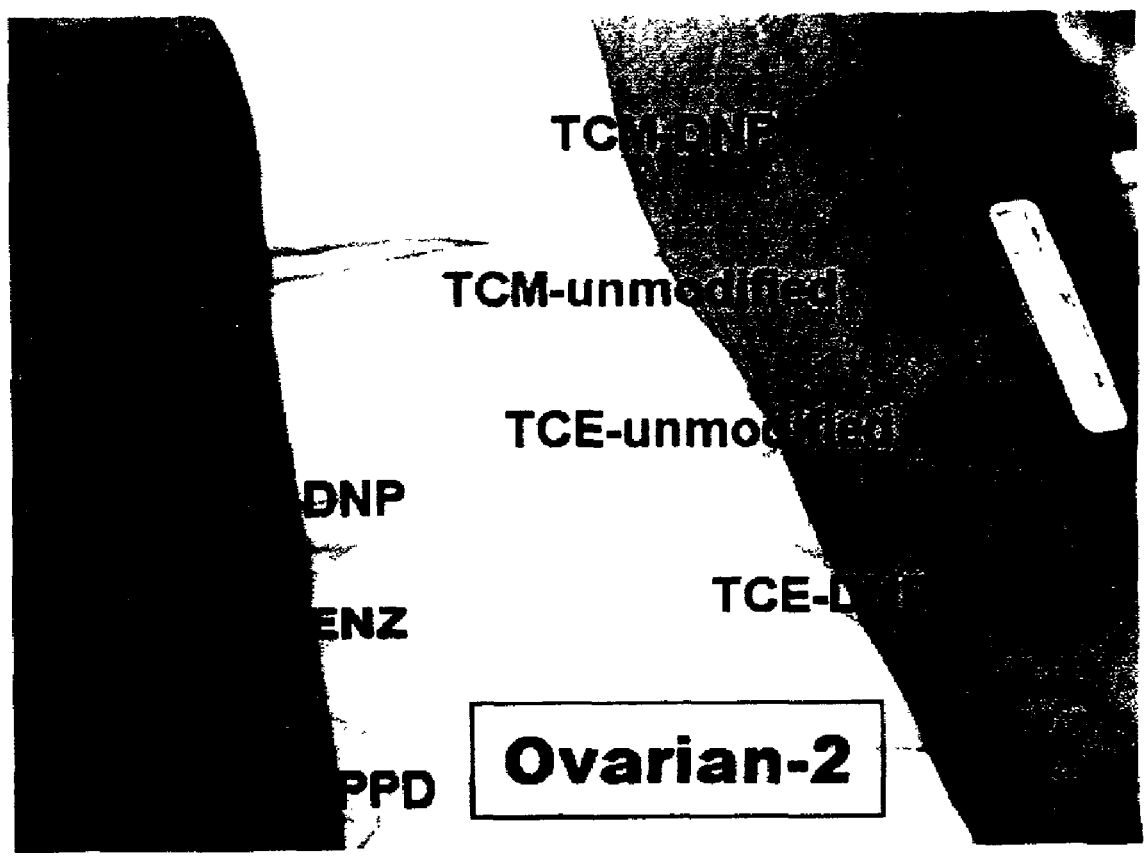
FIG. 1 displays a delayed type hypersensitivity response on the arms of ovarian cancer patient number 2. TCM-DNP=mechanically dissociated tumor cells which have been haptenized (modified) with DNP, TCM-unmodified=mechanically dissociated tumor cells which have not been modified, TCE-DNP=enzymatically dissociated tumor cells which have been haptenized with DNP, TCE-unmodified=enzymatically dissociated tumor cells which have not been modified, and the controls: LY-DNP=the patient's own lymphocytes, LY-ENZ=the patient's own lymphocytes together with collagenase and DNase, enzymes used in the enzymatic dissociation of tumor cells, LY=the patient's own lymphocytes alone, and PPD (purified protein derivative)=a positive tuberculosis control.
Figure 2:
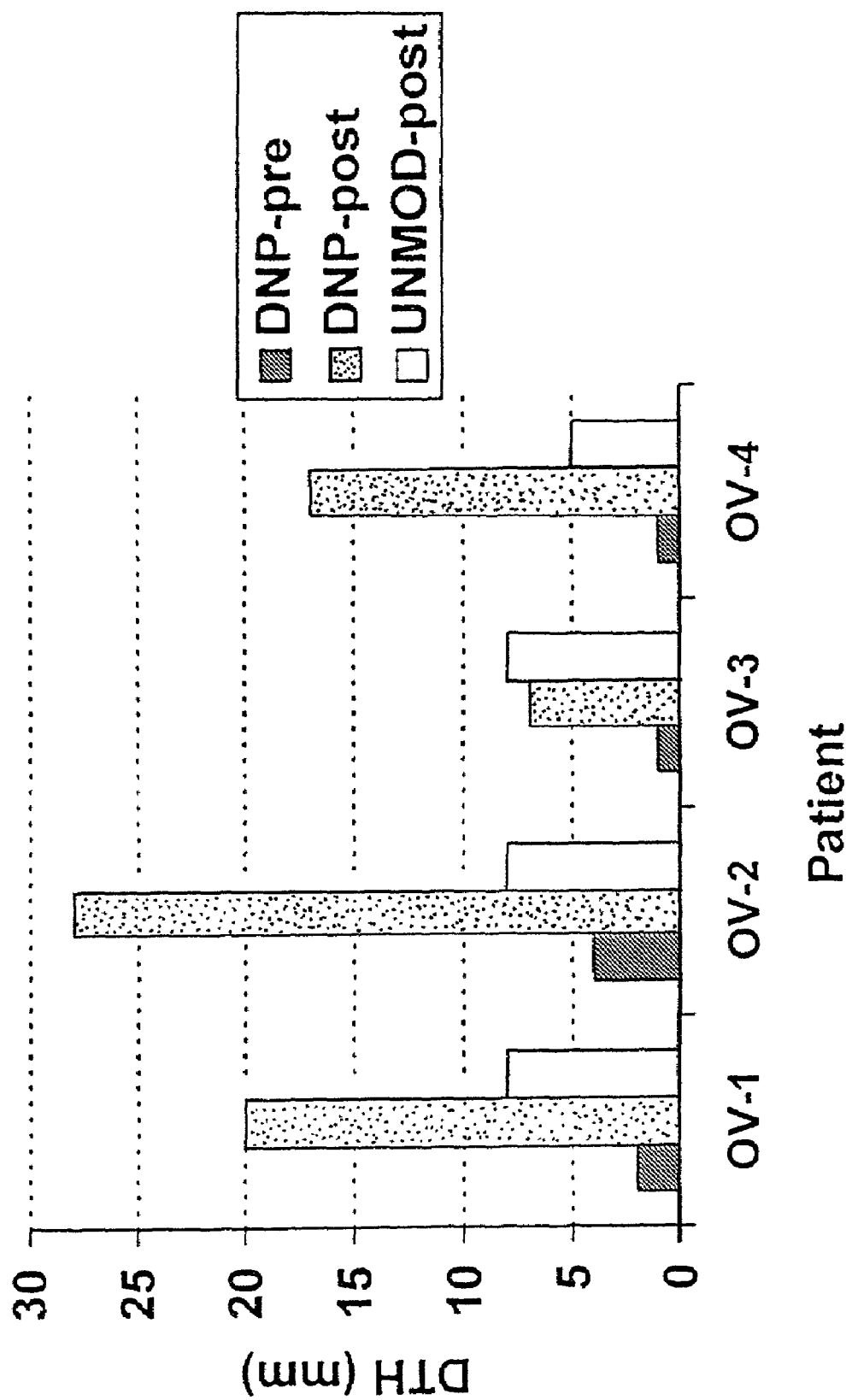
FIG. 2 sets forth a graph of a delayed-type hypersensitivity (DTH) response of four ovarian cancer patients. Prior to treatment, the patients were skin tested for DTH to DNP modified autologous ovarian tumor cells (DNP-pre). Following the administration of six vaccines, one delivered weekly over six weeks, the patients were again skin tested for DTH to DNP modified autologous ovarian tumor cells (DNP-post) and also to unmodified ovarian tumor cells (UNMOD-post).

The present invention is directed to cancer immunotherapy. A novel tumor composition and methods of treating cancer are included in the scope of the invention.

The present invention is directed for use in treating cancer, including metastatic and primary cancers. Cancers treatable with the present invention include solid, including carcinomas, and non-solid, including hematologic malignancies, tumors. Carcinomas include and are not limited adenocarcinomas and epithelial carcinomas. Hematologic malignancies include leukemias, lymphomas, and multiple myelomas. The following are non-limiting examples of the cancers treatable with the composition and methods of the present invention: ovarian, including advanced ovarian, leukemia, including and not limited to acute myelogenous leukemia, colon, including colon metastasized to liver, for example, rectal, colorectal, melanoma, breast, lung, breast, kidney, and prostate cancers.

The ovarian cancers may be adenocarcinomas or epithelial carcinomas. Colon and prostate cancer are adenocarcinomas. Leukemias may originate from myeloid cells of the bone marrow or lymphocytic cells of the bone marrow or lymph nodes. Leukemias may be acute, exhibited by maturation arrest at a primitive stage of development, and chronic, exhibited by excess accrual of mature lymphoid or myeloid cells.

Stage I, II, III, or IV cancer may be treated with the compositions and methods of the present invention, preferably stages III and IV, even more preferably stage III. Mammals, particularly humans, having metastatic cancer of the foregoing type may be treated with the compositions and methods of the present invention.

Tumor Cells

The compositions of the present invention are prepared from tumor cells. Included within the definition of tumor cell for purposes of the present invention are whole and disrupted tumor cells as well.

The tumor cells of the present invention may be live, attenuated, or killed cells. Tumor cells which are not going to grow and divide after administration into the subject such that they are substantially in a sate of no growth are preferred for use in the present invention. It is to be understood that "cells in a state of no growth" means live or killed, whole or disrupted (or both whole and disrupted) cells that will not divide in vivo. Conventional methods of suspending cells in a state of no growth are known to skilled artisans and may be useful in the present invention. For example, cells may be irradiated prior to use such that they do not grow. Tumor cells may be irradiated at 2500 cGy to prevent the cells from growing after administration.

The tumor cells of the same type as, and are preferably syngeneic (e.g. autologous) to, the cancer which is to be treated. For purposes of the present invention, syngeneic refers to tumor cells that are genetically identical. For example, genetic identity may be determined with respect to antigens or immunological reactions, and any other methods known in the art. Preferably the cells originate from the type of cancer which is to be treated, and more preferably, from the same patient who is to be treated. The tumor cells may be, and are not limited to, autologous cells dissociated from biopsy specimens or tissue culture. Nonetheless, allogeneic cells and stem cells are also within the scope of the present invention.

The compositions of the invention may be employed in the method of the invention singly or in combination with other compounds, including and not limited to other compositions of the invention. Accordingly, tumor cells and tumor cell extracts (such as disrupted tissue or cells) may be used alone or co-administered. For purposes of the present invention, co-administration includes administration together and consecutively. Further, the tumor cells may be co-administered with other compounds including and not limited to cytokines such as interleukin-2, interleukin-4, gamma interferon, interleukin-12, GM-CSF. The tumor cells of the invention may also be used in conjunction with other cancer treatments including and not limited to chemotherapy, radiation, antibodies, and antisense oligonucleotides. However, it is a goal of the present invention to be useful alone as a cancer treatment, such that the need for additional therapies will be unnecessary.

The compositions of the invention may be administered in a mixture with a pharmaceutically-acceptable carrier, selected with regard to the intended route of administration and the standard pharmaceutical practice. Dosages may be set with regard to weight, and clinical condition of the patient. The proportional ratio of active ingredient to carrier naturally depend on the chemical nature, solubility, and stability of the compositions, as well as the dosage contemplated. Amounts of the tumor cells of the invention to be used depend on such factors as the affinity of the compound for cancerous cells, the amount of cancerous cells present and the solubility of the composition. The compounds of the present invention may be administered by any suitable route, including inoculation and injection, for example, intradermal, intravenous, intraperitoneal, intramuscular, and subcutaneous.

In a preferred embodiment of the invention, the composition comprises a vaccine consisting of about $10 \times 10^6$ to about $25 \times 10^6$, more preferably about $5 \times 10^6$ to about $25 \times 10^6$, live, irradiated, tumor cells suspended in a pharmaceutically acceptable carrier or diluent, such as and not limited to Hanks solution, saline, phosphate-buffered saline, and water. The composition may be administered by intradermal injection into 3 contiguous sites per administration on the upper arms or legs, excluding limbs ipsilateral to a lymph node dissection.

Hapten

The tumor cells of the composition of the present invention may be employed as modified, unmodified, or a combination of modified and unmodified tumor cells. For purposes of the present invention, modified includes and is not limited to modification with a hapten. For purposes of the present invention, virtually any small protein or other small molecule that does not alone induce an immune response (but that enhances immune response against another molecule to which it is conjugated or otherwise attached) may function as a hapten. A variety of haptens of quite different chemical structure have been shown to induce similar types of immune responses: TNP (Kempkes et al., *J Immunol.* 1991 147:2467); phosphorylcholine (Jang et al., *Eur. J. Immunol.* 1991 21:1303); nickel (Pistoor et al., *J Invest. Dermatol.* 1995 105:92); arsenate—Nalefski and Rao, *J. Immunol.* 1993 150:3806). Conjugation of a hapten to a cell to elicit an immune response may preferably be accomplished by conjugation via ∈-amino groups of lysine or —COOH groups. This group of haptens include a number of chemically diverse compounds: dinitrophenyl, trinitrophenyl, N-iodoacetyl-N'-(5-sulfonic 1-naphthyl) ethylene diamine, trinitrobenzenesulfonic acid, fluorescein isothiocyanate, arsenic acid benzene isothiocyanate, trinitrobenzenesulfonic acid, phosphorylcholene, sulfanilic acid, arsanilic acid and dinitrobenzene-S-mustard (Nahas and Leskowitz, *Cellular Immunol.* 1980 54:241). Once armed with the present disclosure, skilled artisans, would be able to choose haptens for use in the present invention.

Dinitrophenyl, a representative of haptens in general, may be used to immunize patients to the chemical dinitrophenyl (DNP) by application of dinitrofluorobenzene (DNFB) to the skin. Subsequently, (about two weeks later, for example) the patients may then be injected with a tumor cell composition. The composition may be administered (such as my reinjection) every 4 weeks eight treatments. The immune response of the patient may be augmented with drugs. For example, cyclophosphamide (CY) may be administered prior to each administration.

Adjuvant

In another preferred embodiment, a tumor cell composition may be administered with an immunological adjuvant. While commercially available pharmaceutically acceptable adjuvants are limited, representative examples of adjuvants include Bacille Calmette-Guerin, BCG, or the synthetic adjuvant, QS-21 comprising a homogeneous saponin purified from the bark of *Quillaja saponaria*, *Corynebacterium parvum*, McCune et al., *Cancer* 1979 43:1619, and IL-12.

It will be understood that the adjuvant is subject to optimization. In other words, the skilled artisan can engage in no more than routine experimentation and determine the best adjuvant to use.

Methods of Making the Present Invention

The tumor cells for use in the present invention may be prepared as follows. Tumors are processed as described by Berd et al. (1986), supra, incorporated herein by reference in its entirety. The cells are extracted by dissociation, such as by enzymatic dissociation with collagenase and DNase, or by mechanical dissociation such as with a blender, teasing with tweezers, mortar and pestle, cutting into small pieces using a scalpel blade, and the like.

The dissociated cells may be stored frozen, such as in a controlled rate freezer or in liquid nitrogen until needed. The cells are ready for use upon thawing. Preferably, the cells are thawed shortly before the cells are to be administered to a patient. For example, on the day that a patient is to be skin tested or treated, the cells may be thawed. Optionally, the cells may be washed, and optionally irradiated to 2500 R. They may be washed again and then suspended in Hanks balanced salt solution without phenol red.

Modification of the prepared cells with DNP or another hapten may be performed by known methods, e.g. by the method of Miller and Clanian, *J. Immunol.*, 1976, 117, 1519, incorporated herein by reference in its entirety, which involves a 30 minute incubation of tumor cells with DNFB under sterile conditions, followed by washing with sterile saline.

Methods of Using the Present Invention

In the methods of the present invention, a method of treating a patient diagnosed with or suspected of having cancer of the foregoing type, comprises administering a pharmaceutically acceptable amount of a composition selected from the group consisting of live tumor cells. The composition may be mixed with an immunological adjuvant and/or a pharmaceutically acceptable carrier. A pharmaceutically acceptable amount of a low-dose cyclophosphamide or another lowdose chemotherapy may be administered preceding the administration of the composition. The haptenized composition may optionally be followed by administration of a pharmaceutically acceptable amount of a non-haptenized vaccine. A non-haptenized composition may also be administered in accordance with the methods of the present invention.

The present invention is useful following conventional treatment for cancer, such as surgery. The tumor may be optimally or sub-optimally debulked. Optimally debulked refers to excising the tumor and small tumor pieces remain in the patient. Sub-optimally debulked refers to excising the tumor and large pieces remain in the patient. In the case of non-solid tumors, an appropriate blood or bone marrow sample can be collected, and cancer cells are isolated by known techniques.

Human cancer vaccines have been developed and tested by, a number of workers. Although they can sometimes induce weak immunity to a patient's cancer, they rarely cause tumor regression or prolong survival. The development of inflammatory responses in metastatic tumors was surprisingly found with the vaccine of the present invention. The tumor becomes reddened, warm and tender. Ultimately, in a substantial number of cases, the tumor regresses to the extent that the tumor disappears, to the naked eye and microscopically. Microscopically, infiltration of T lymphocytes into the tumor mass is observed. Therefore, this approach, which increases the inflammatory response and the number and capacity of lymphocytes entering the tumor, is a significant advance in the art.

The effectiveness of the vaccine may be improved by adding various, biological response modifiers. These agents work by directly or indirectly stimulating the immune response. Biological response modifiers of the present invention include and are not limited to interleukin-12 and gamma interferon. In this embodiment, IL12 will be given following the each vaccine injection. Administration of IL12 to patients with inflammatory responses causes the T lymphocytes within the tumor mass to proliferate and become more active. The increased T cell numbers and functional capacity leads to immunological destruction of the tumors. Dosages for IL12 will be prepared in accordance with the dosage indications set forth above.

The invention is further illustrated by means of the following actual Example 1 prophetic Examples 2-4 which are meant to be illustrations only and are not intended to limit the present invention to these specific embodiments.

EXAMPLE 1

Ovarian Carcinoma

Patients with stage III disease constitute an ideal study system for active immunotherapy, because: 1) Large amounts of tumor tissue can be obtained at the time of debulking surgery; 2) Combination chemotherapy (e.g., carboplatin+taxol) can further reduce the tumor burden; 3) Following chemotherapy, patients are clinically tumor-free with excellent performance status; and 4) Most of these patients (up to 80%) develop recurrence and die, which underscores the need for an adjunctive therapy, such as a vaccine. Following suboptimal surgical debulking and chemotherapy, the median times to tumor recurrence and death are 18 months and 37 months, respectively.

Some evidence has accumulated that human ovarian carcinoma may be immunogenic and a suitable target for immunotherapy. T lymphocytes obtained from malignant ascitic fluid can specifically lyse ovarian carcinoma cells (Ferrini et al.; Vaccarello et al.). Ovarian cancer-associated antigens have been identified (Ioannides et al.; Greiner et al.). It is of interest that some ovarian cancers express the MAGE antigens, originally described on melanoma cells (Yamada et al.). Finally, several investigators have attempted to use vaccine to treat ovarian carcinoma (Mobus et al.; Mallmann et al.; Bowen-Yacyshyn et al.; Maclean et al.). No well defined clinical responses have been documented, but immunological responses to the vaccines have been measured (Maclean et al.).

The objectives are to treat patients with advanced adenocarcinoma of the ovary with autologous tumor cells modified with the hapten, DNP to determine whether patients develop delayed-type hypersensitivity (DTH) to autologous carcinoma cells and to assess toxicity.

Patients with stage III adenocarcinoma. of the ovary were initially treated according to standard medical practice (debulking surgery followed by chemotherapy). After the completion of chemotherapy, they received a six week course of treatment with a vaccine consisting of autologous, irradiated ovarian carcinoma cells modified with the hapten, dinitrophenyl (DNP). Low dose cyclophosphamide will be administered prior to the first vaccine injection. After the completion of the course of vaccine they, were tested for delayed type hypersensitivity to autologous carcinoma cells, both DNP-modified and unmodified. In vitro studies were performed with cryopreserved lymphocytes extracted from metastatic tumors and/or separated from peripheral blood.

Patients were selected for inclusion in the study if they had stage III adenocarcinoma of the ovary and surgical debulking. The mass of tumor excised from each patient was sufficient to obtain at least $100 \times 10^6$ viable tumor cells. They received chemotherapy with carboplatin+taxol and were clinically tumor-free following completion of chemotherapy (i.e., normal physical examination and CT studies and serum CA-125<35 IU/L. Patients were excluded from this specific study for the following: insufficient quantity of tumor-cells for vaccine and skin-testing ($<100 \times 10^6$ cells), Karnovsky performance status less than 80, major field radiation therapy within the preceding 6 months, current administration of systemic corticosteroids, hematocrit<30% or WBC<3000, age<18, active autoimmune disease, active, serious infection, another active malignancy other than squamous cell carcinoma of skin, in situ carcinoma of the cervix, or superficial bladder carcinoma, evidence of infection with hepatitis B virus (circulating antigen) or with HIV (circulating antibody), or inability to give informed consent.

Surgery and Tumor Acquisition

Patients underwent surgical resection of the ovarian cancer+bilateral salpingo-ovariectomy+debulking of peritoneal metastases. Patients who underwent either optimal or suboptimal debulking were eligible for the study. Tumor tissue was delivered to the laboratory and processed to obtain single cell suspensions (see below). The cells were cryopreserved and stored in liquid nitrogen.

Chemotherapy

Beginning within 6 weeks after surgery all patients began chemotherapy with carboplatin or cisplatin+taxol, according to the following dosage-schedule:

carboplatin AUC 7.5 or cisplatin 75 mgM$^2$—every 3 weeks
taxol 175 mg/M$^2$ IV over 3 hours—every 3 weeks Six cycles of chemotherapy were administered. Any other chemotherapy could have been administered.

Vaccine Administration—Approximately, four weeks after completion of chemotherapy, patients underwent a metastatic evaluation to include computer tomography (CT) chest-abdomen-pelvis. Only patients with no evidence of recurrent carcinoma were eligible for vaccine treatment. Patients with elevated serum level of CA125 were eligible providing that CT studies were negative for recurrence. The vaccine program was started at least 4 weeks after, and no more than 12 weeks after, the last administration of chemotherapy.

On day-7, patients were skin-tested with: 1) autologous ovarian carcinoma cells modified with DNP (OV-DNP), 2) diluent (Hanks balanced salt solution with 0.1% human albumen, and 3) PPD intermediate. DTH reactions were measured on day-5. On day 0 (Monday), patients received cyclophosphamide 300 mg/M$^2$ as a rapid IV infusion. Three days later (Thursday) they were injected intradermally with autologous ovarian carcinoma vaccine and this was repeated weekly for 6 weeks. Vaccines consisted of DNP-modified, autologous ovarian carcinoma cells mixed with BCG. Vaccines were injected into the upper arm. If for some reason a left axillary lymph node dissection had been performed, the right arm was used.

Two and a half weeks after the sixth vaccine, patients underwent clinical evaluation, consisting of CBC, SMA-12, CA125, and chest x-ray. They were tested for DTH to the following materials: autologous ovarian carcinoma cells, both DNP-modified and unmodified; autologous peripheral blood lymphocytes, both DNP-modified and unmodified; diluent; and PPD intermediate. Also, they were tested for contact sensitivity to dinitrofluorobenzene (DNFB). A complete clinical evaluation with CT or MRI studies are in progress for two of the patients, and were begun five months after the start of the vaccine program.

Booster Injections

Patients who remained relapse-free will be given a seventh (booster) vaccine at the six month point (measured from beginning the vaccine program). For each patient at least one cryopreserved vial of tumor cells will be saved for the six-month booster injection. If the number of cells available is anticipated to be insufficient for 6 weekly vaccines plus the six-month booster, then the initial course of weekly injections will be reduced to 5, but no fewer. Another booster vaccine will be administered in one year, but only if a sufficient number of cells is available. Just prior to the one-year booster, patients will be skin-tested with autologous tumor cells to determine whether their previous level of immunity has been maintained.

Vaccine Preparation

Tumor masses were processed as previously described (Berd et al., 1986, U.S. Pat. No. 5,290,551, and applications U.S. Ser. Nos. 08/203,004, 08/479,016, and corresponding PCT application PCT/US96/09511, each incorporated herein by reference in their entirety). Cells were extracted by enzymatic dissociation with collagenase and DNase and by mechanical dissociation, frozen in a controlled rate freezer, and stored in liquid nitrogen until needed. On the day that a patient was to be treated, the cells were thawed, washed, and irradiated to 2500 R. Then they were washed again and suspended in Hanks balanced salt solution without phenol red.

Modification of tumor cells with DNP was performed by the method of Miller and Claman (1976). This involves a 30 minute incubation of tumor cells with dinitrofluorobenzene (DNFB) under sterile conditions, followed by washing with sterile saline.

The vaccine consisted of a minimum of $2.5 \times 10^6$ trypan-blue-excluding tumor cells, and a maximum of $7.5 \times 10^6$ tumor cells suspended in 0.2 ml Hanks solution. Each vaccine treatment consisted of three injections into contiguous sites.

BCG Doses

The first and second vaccines were mixed with 0.1 ml of a 1:10 dilution of Tice BCG ("Tice-1"). The third and fourth vaccines were mixed with 0.1 ml of a 1:100 dilution ("Tice-3"). The fifth and sixth and booster vaccines were mixed with 0.1 ml of a 1:1000 dilution ("Tice-5") The ideal vaccine reaction is an inflammatory papule with no more than small (<5 mm) central ulceration.

Skin-Testing

Skin testing was performed by the intradermal injection of 0.1 ml of test material on the forearm, and DTH was assessed at 48 h by measuring the mean diameter of induration. The following materials were tested: 1) $1 \times 10^6$ irradiated autologous ovarian cancer cells unmodified and modified with DNP; both enzymatically-dissociated (TCE) and mechanically-dissociated (TCM) tumor cells will be used; 2) $3 \times 10^6$ autologous peripheral blood lymphocytes unmodified and modified with DNP; 3) Hanks solution; and 4) PPD-intermediate strength. Also, contact sensitivity to DNFB was tested by applying 200 µg to the skin of the ventral surface of the upper arm and examining the area for a circle of induration at 48 hours. The full battery of DTH tests was performed following the six week course of vaccine administration. Pretreatment DTH testing was limited to DNP-modified ovarian cancer cells, PPD, and diluent. This strategy is designed to avoid: 1) sensitizing patients to DNP-modified lymphocytes and 2) tolerizing patients by injection of unmodified tumor cells.

All patients had blood collected for separation and cryopreservation of lymphocytes and serum each time skin-testing is performed. Periodically, these were tested for: response to autologous ovarian cancer cells, as measured by proliferation, cytokine release, and cytotoxicity.

Patients were evaluated for metastatic disease before vaccine therapy began. After the end of the first eight weeks of vaccine therapy, evaluations were performed every three months. Evaluations will continue through year 02, every four months in year 03, and every six months thereafter. Physical examination and routine bloodwork (CBC, SMA-12, and CA125) will be performed with each evaluation. CT of the chest-abdomen-pelvis were performed prior to the administration of vaccine, at 6 months and 12 months (before vaccine boosters), and then as clinically indicated. Relapse-free and total survival will be measured. All patients will be followed for at least five years or until time of death.

Pharmaceutical Information

BCG—This is the Tice strain (substrain of the Pasteur Institute strain) obtained from Organon Teknika Corporation (Durham, N.C.). The freeze-dried material was reconstituted with 1 ml sterile water or phosphate buffered saline, pH 7.2 (PBS). Appropriate dilutions were made in sterile buffered saline. Then 0.1 ml was drawn up and mixed with the vaccine just before injection.

Cyclophosphamide—This was reconstituted in sterile water and the proper dosage is administered by rapid IV infusion.

Toxicity

Cyclophosphamide—Typically, about one third of patients experience nausea and about 10% have vomiting after low dose cyclophosphamide. Leukopenia, alopecia, and cystitis do not occur at this dose. It is expected that this protocol will be associated with a lower incidence of nausea and vomiting than previous protocols, since cyclophosphamide will be administered only once in association with the final vaccine inoculation. None of the six patients experienced reactions to cyclophosphamide.

Vaccine—All patients develop a local reaction to BCG, consisting of a draining, tender pustule that heals in 2-3 months leaving a smallpox vaccination-like scar. As patients develop sensitivity to BCG, the intensity of these reactions increases. Anaphylaxis, other allergic phenomena, and autoimmunity have never been observed. It is theoretically possible that injected tumor cells could grow in a patient's skin. However, this has not been observed in more than 200 patients injected with vaccines, prepared similarly to the vaccine of the present invention, to various cancers to date and is considered a very remote possibility.

Reactions at the vaccine sites were graded as follows:
  0—no symptoms
  1—itching or discomfort, but no interference with arm movement or normal activity
  2—discomfort causing interference with arm movement, but not requiring modification of normal-activity
  3—discomfort causing major interference with arm movement and requiring modification of normal activity, and
  4—discomfort causing inability to use the extremity for normal activity.

DNP—As noted above, a large number of patients have been sensitized to DNCB over the past 18 years (Eilber and Morton; Berd et al., 1982, 1984) without ill effects. About 200 patients injected with autologous melanoma cells modified with DNP by the method described above exhibited no significant toxicities, except for the development of an urticarial eruption in a single patient, which cleared spontaneously within 5 days.

Precautions to be Taken—Patients were observed following injection of the vaccine. Patients experiencing unexpected symptoms or signs were instructed to contact the physician and were evaluated immediately. Fever that causes discomfort was treated with acetaminophen. Nausea caused by low dose cyclophosphamide was treated with oral prochlorperazine (Compazine). If severe local reactions (>5 mm ulceration) occurred at the vaccine site, subsequent doses of BCG were reduced (see above). No side effects were experienced by the six patients.

Duration of Study

1) Patients who are relapse-free at the 1 year evaluation will receive a final booster injection of vaccine. Then they will be followed without further treatment.

2) Patients who develop metastases will be taken off study and treated as clinically indicated (usually surgery or chemotherapy).

All Thomas Jefferson University, NIH, and FDA regulations regarding informed consent were followed in regard to informed consent.

Statistical Considerations

The major endpoint is the development of DTH to DNP-modified autologous tumor cells. In our studies of DNP-modified autologous vaccine for melanoma, 100% of patients (N=60) developed a positive DTH response ($\geq 5$ mm diameter of induration) to DNP-modified autologous tumor cells following treatment, and 85% developed a large positive response ($\geq 10$ mm diameter of induration). This study is to determine whether at least 50% of ovarian carcinoma patients develop a positive response ($\geq 5$ mm) to DNP-modified autologous ovarian carcinoma cells.

An efficacy study to determine whether DNP-vaccine prolongs relapse-free and/or total survival in these patients is also planned. We will measure survival parameters in the current study (Kaplan-Meier method). A striking improvement in two-year relapse-free survival (e.g., from the expected 20% to 60%) would be highly encouraging. Since Thomas Jefferson University Hospital treats about 40 stage III ovarian carcinoma patients yearly, we expect that accrual of patients to be completed soon.

Results

Six patients have been entered onto the study and results are available for the first four patients.

| Patient | Pre/Post Vaccine | DNP-modified tumor cells | Unmodified tumor cells | Unmodified lymphocytes |
|---------|------------------|--------------------------|------------------------|------------------------|
| OV-1 | PRE | 2 | nd | nd |
| OV-1 | POST | 20 | 8 | 0 |
| OV-2 | PRE | 4 | nd | nd |
| OV-2 | POST | 28 | 8 | 0 |
| OV-3 | PRE | 0 | nd | nd |
| OV-3 | POST | 7 | 8 | 0 |
| OV-4 | PRE | 0 | nd | nd |
| OV-4 | POST | 17 | 5 | 0 |

Delayed-Type Hypersensitivity (DTH) (Mm induration)

nd = not done

Thus, following administration of DNP-modified autologous ovarian carcinoma vaccine, 4/4 patients developed DTH to DNP-modified and to unmodified autologous ovarian carcinoma cells. To Applicant's knowledge, this is the first demonstration of induction of cell-mediated immunity to autologous ovarian cancer cells in humans.

EXAMPLE 2

Advanced Ovarian Carcinoma

The objectives of the study are to treat patients with advanced adenocarcinoma of the ovary with autologous tumor cells modified with the hapten, DNP, and to determine whether patients develop delayed-type hypersensitivity (DTH) to autologous carcinoma cells, and to assess toxicity.

Patients with metastatic adenocarcinoma of the ovary (stage III or IV) who cannot be cured surgically and who have failed or ceased to respond to conventional chemotherapy, but who have good performance status, will be the study subjects. All patients must have received standard first-line chemotherapy (usually taxol and cisplatin or carboplatin). Also, patients must have failed to respond (or ceased to respond) to one or two second-line chemotherapies. After clinical and immunological evaluation, they will receive a six week course of treatment with a vaccine consisting of autologous, irradiated carcinoma cells modified with the hapten, dinitrophenyl (DNP). Low dose cyclophosphamide will be administered prior to the first vaccine injection. After the completion of the course of vaccine they, will be tested for delayed type hypersensitivity to autologous carcinoma cells, both DNP-modified and unmodified.

Patients will be eligible if they have stage III or stage IV adenocarcinoma of the ovary that is surgically incurable. All patients must have received standard first-line chemotherapy (usually taxol and cisplatin or carboplatin). Also, patients must have failed to respond (or ceased to respond) to one or two second-line chemotherapies. All patients must either: 1) be candidates for surgical debulking, with resection of tumor sufficient to obtain at least $100\times10^6$ viable tumor cells; or 2) have ascites with sufficient concentration of tumor cells to allow harvesting of at least $100\times10^6$ viable tumor cells with a single paracentesis.

Patients will be excluded for the following reasons: an insufficient quantity of tumor cells for vaccine and skin-testing ($<100\times10^6$ cells), Karnovsky performance status less than 70, major field radiation therapy within the preceding 6 months, current administration of systemic corticosteroids, hematocrit<30% or WBC<3000, age<18, active autoimmune disease, active, serious infection, another active malignancy other than squamous cell carcinoma of skin, in situ carcinoma of the cervix, or superficial bladder carcinoma, evidence of infection with hepatitis B virus (circulating antigen) or with HIV (circulating antibody), or inability to give informed consent.

Surgery and Tumor Acquisition

Patients will undergo surgical debulking of one or more metastatic masses. Tumor tissue will be delivered to the laboratory and processed to obtain single ce suspensions (see below). Alternatively, patients with ascites will undergo paracentesis of 500-2000 ml. Tumor cells will be obtained by centrifugation. In either case, the cells will be cryopreserved and stored in liquid nitrogen.

Vaccine Administration

Following surgery or paracentesis, patients will undergo a metastatic evaluation to include CT chest-abdomen-pelvis. The vaccine program will be started within 4 weeks of surgery and within 2 weeks of paracentesis.

On day −7, patients will be skin-tested with: 1) autologous ovarian carcinoma cells modified with DNP (OV-DNP), 2) diluent (Hanks balanced salt solution with 0.1% human albumen, and 3)PPD intermediate. DTH reactions will be measured on day −5. On day 0 (Monday), patients will receive cyclophosphamide 300 mg/M$^2$ as a rapid IV infusion. Three days later (Thursday) they will be injected intradermally with autologous ovarian carcinoma vaccine and this will be repeated weekly for 6 weeks. All vaccines will consist of DNP-modified, autologous ovarian carcinoma cells mixed with BCG. All vaccines will be injected into the left upper arm. (If for some reason a left axillary lymph node dissection had been performed, the right arm will be used.)

Two and a half weeks after the sixth vaccine, patients will undergo clinical evaluation, consisting of CBC, SMA-12, CA125, chest x-ray, and CT studies as indicated. They will be tested for DTH to the following materials: autologous ovarian carcinoma cells, both DNP-modified and unmodified; autologous peripheral blood lymphocytes, both DNP-modified and unmodified; diluent; and PPD intermediate. Also, they will be tested for contact sensitivity to dinitrofluorobenzene (DNFB). A complete clinical evaluation with CT or MRI studies will be performed 3 and 6 months after the start of the vaccine program. Patients who have an objective response or stable disease, will be given a seventh (or booster) vaccine six months after beginning the vaccine program. Another booster injection will be given at the one-year point to patients with responding or stable disease for whom sufficient numbers of cryopreserved tumor cells are available.

Vaccine Preparation

Tumor masses obtained from laparotomy will be processed as previously described (Berd et al., 1986). Cells will be extracted by enzymatic dissociation with collagenase and DNase and by mechanical dissociation. Tumor cells will extracted from ascites by centrifugation and repeated washing in saline; if necessary, erythrocytes will be removed by gradient centrifugation on Ficoll-hypaque.

Cells obtained by either of these two methods will frozen in a controlled rate freezer, and stored in liquid nitrogen until needed. On the day that a patient is to be treated, the cells will be thawed, washed, and irradiated to 2500 R. Then they will be washed again and suspended in Hanks balanced salt solution without phenol red.

Modification of tumor cells with DNP will be performed by the method of Miller and Claman (1976). This involves a 30 minute incubation of tumor cells with dinitrofluorobenzene (DNFB) under sterile conditions, followed by washing with sterile saline.

The vaccine consists of a minimum of $2.5\times10^6$ trypan-blue-excluding tumor cells, and a maximum of $7.5\times10^6$ tumor cells suspended in 0.2 ml Hanks solution. Each vaccine treatment will consist of three injections into contiguous sites.

BCG Doses

The first and second vaccines will be mixed with 0.1 ml of a 1:10 dilution of Tice BCG ("Tice-1"). The third and fourth vaccines will be mixed with 0.1 ml of a 1:100 dilution ("Tice-3"). The fifth and sixth and booster vaccines will be mixed with 0.1 ml of a 1:1000 dilution ("Tice-5"). The ideal vaccine reaction is an inflammatory papule with no more than small (<5 mm) central ulceration. If reactions are larger than this, the dose of BCG will be further decreased. Patients who have a positive PPD ($\geqq$5 mm induration) prior to receiving vaccine will have the initial dose reduced to 0.1 ml of a 1:100 dilution; subsequent doses will be determined by the previous reactions.

Skin-testing

Skin-testing will be performed by the intradernial injection of 0.1 ml of test material on the forearm, and DTH will be assessed at 48 h by measuring the mean diameter of induration. The following materials will be tested: 1)$1\times10^6$ irradiated autologous ovarian cancer cells unmodified and modified with DNP; both enzymatically-dissociated (TCE) and mechanically-dissociated (TCM) tumor cells will be used; 2)$3\times10^6$ autologous peripheral blood lymphocytes unmodified and modified with DNP; 3)Hanks solution; 4)PPD-intermediate strength. Also, contact sensitivity to DNFB will be tested by applying 200 ug to the skin of the ventral surface of the upper arm and examining the area for a circle of induration at 48 hours. The full battery of DTH tests will be performed following the six week course of vaccine administration. Pre-treatment DTH testing will be limited to DNP-modified ovarian cancer cells, PPD, and diluent. This strategy is designed to avoid: I)sensitizing patients to DNP-modified lymphocytes and 2)tolerizing patients by injection of unmodified tumor cells.

All patients will have blood collected for separation and cryopreservation of lymphocytes and serum each time skin-testing is performed (see Schema for schedule of blood drawing). If funding is available, these will be tested for: response to autologous ovarian cancer cells, as measured by proliferation, cytokine release, and cytotoxicity.

This is a phase I study to assess immunological response and toxicity. Although it is not an objective of this study to measure anti-tumor response rate, patients with measurable metastases will be evaluated for tumor response by standard criteria: complete response=disappearance of all evident metastatic disease for at least 3 months; partial response=decrease in the mean diameter of a measurable mass by 50% or more for at least 3 months without simultaneous growth of other metastases; mixed response=decrease in the mean diameter of a measurable mass by 50% or more for at least 3 months but with simultaneous growth of other metastases; no response=no tumor regression as defined above.

When possible, patients will also be evaluated for development of inflammatory response in metastatic masses by biopsy performed post-vaccine treatment. Because metastases are likely to be intra-abdominal, the opportunities for such biopsies will be limited. It is anticipated that patients who have stable or regressing metastases following vaccine will be candidates for laparoscopic biopsy to determine if tumor inflammatory responses have been induced. Patients with ascites will undergo paracentesis following a course of vaccine treatment. The cell composition of ascitic fluid post-vaccine will be compared with that pre-vaccine. It is hypothesized that post-vaccine ascites will contain increased numbers of T lymphocytes.

Pharmaceutical Information

BCG

This is the Tice strain (substrain of the Pasteur Institute strain) obtained from Organon Teknika Corporation (Durham, N.C.). The freeze-dried material is reconstituted with 1 ml sterile water or phosphate buffered saline, pH 7.2 (PBS). Appropriate dilutions are made in sterile buffered saline. Then 0.1 ml is drawn up and mixed with the vaccine just before injection.

Cyclophosphamide

This is reconstituted in sterile water and the proper dosage is administered by rapid IV infusion.

Toxicity

Cyclophosphamide

About one third of patients experience nausea and about 10% have vomiting after low dose cyclophosphamide. Leukopenia, alopecia, and cystitis do not occur at this dose. It is expected that this protocol will be associated with a lower incidence of nausea and vomiting than previous protocols, since cyclophosphamide will be administered only once.

Vaccine

All patients develop a local reaction to BCG, consisting of a draining, tender pustule that heals in 2-3 months leaving a smallpox vaccination-like scar. As patients develop sensitivity to BCG, the intensity of these reactions increases. Anaphylaxis, other allergic phenomena, and auto-immunity have never been observed. It is theoretically possible that injected tumor cells could grow in a patient's skin. However, this has not been observed in more than 200 patients injected so far and is considered a very remote possibility.

Reactions at the vaccine sites will be graded as follows:

0—no symptoms

1—itching or discomfort, but no interference with arm movement or normal activity 2—discomfort causing interference with arm movement, but not requiring modification of normal activity 3—discomfort causing major interference with arm movement and requiring modification of normal activity, and 4—discomfort causing inability to use the extremity for normal activity.

DNP

As noted above, a large number of patients have been sensitized to DNCB over the past 18 years (Eilber and Morton; Berd et al., 1982, 1984) without ill effects. We have injected about 200 patients with autologous melanoma cells modified with DNP by the method described above. No significant toxicities have been observed, except for the development of an urticarial eruption in a single patient, which cleared spontaneously within 5 days.

Precautions to be Taken

Patients will be observed following injection of vaccine. Patients experiencing unexpected symptoms or signs will be instructed to telephone and will be evaluated immediately. Fever that causes discomfort will be treated with acetaminophen. Nausea caused by low dose cyclophosphamide will be treated with oral prochlorperazine (Compazine). If severe local reactions (>5 mm ulceration) occur at the vaccine site, subsequent doses of BCG will be reduced (see above).

Duration of Study

The following occurrences will cause a patient to be taken off-study: a) rapid tumor progression requiring major surgery, radiation therapy, administration of corticosteroids, or additional cytotoxic chemotherapy; or b) non-compliance or voluntary withdrawal. Patients with stable or responding metastases will be given a booster injection of vaccine at 6 months, and at 12 months if sufficient numbers of cryopreserved tumor cells are available.

All Thomas Jefferson University, NIH, and FDA regulations regarding informed consent will be followed.

Statistical Considerations

The major endpoint will be the development of DTH to DNP-modified autologous tumor cells. In our studies of DNP-modified autologous vaccine for melanoma, 100% of patients (N=60) developed a positive DTH response ($\geq$5 mm diameter of induration) to DNP-modified autologous tumor cells following treatment, and 85% developed a large positive response ($\geq$10 mm diameter of induration). We would like to determine whether at least 50% of advanced ovarian carcinoma patients develop a positive response ($\geq$5 mm) to DNP-modified autologous ovarian carcinoma cells. Initially, we plan to treat 10 patients. If 9 develop a positive response, then we can conclude with 95% confidence that the response rate exceeds 50%, and the study will be terminated ("positive" result). If <9 but $\geq$5 patients develop a positive response, then an additional 10 patients will be studied. (15/20 positives would have to be observed to be confident that the response is 50%.) If <5 patients develop a positive response, then we will conclude that a 50% response rate cannot be verified unless the sample size is very large ("negative" result).

Patients whose vaccines are prepared from ascitic fluid will be analyzed separately from those whose vaccines are prepared from tumor masses. Thus the total number of patients required for the study will range from 20-40. Since Thomas Jefferson University Hospital treats about 40 stage III ovarian carcinoma patients yearly, we expect that accrual of patients will be completed in less than two years.

It is expected that patients will develop DTH to DNP-modified autologous ovarian carcinoma cells, and that some will develop DTH to unmodified autologous ovarian carcinoma cells as well. No patients are expected to develop DTH to unmodified autologous blood lymphocytes. As a result of DNP-ovarian cancer cell treatment, metastatic tumors will regress and survival of these patients will be prolonged.

EXAMPLE 3

There is circumstantial evidence that AML may be immunogenic in view of the prior experience with AML vaccine using suboptimal techniques. The use of autologous, DNP-modified vaccine has proved successful in melanoma patients with a low tumor burden. Thus, it seems reasonable to use this approach in patients with AML in remission.

The objectives of this study are to determine if the treatment of patients with acute myelogenous leukemia in first or second remission with an autologous DNPmodified leukemia cell vaccine causes 1) significant toxicity, or 2) development of cellmediated immunity to autologous leukemic cells. The study will also measure the duration of remission and survival in these patients.

This is a phase I-II trial to assess toxicity and measure immunological effects. The study subjects will be patients who are in complete remission of acute myelogenous leukemia (AML) (either first or second remission). After induction into remission with standard chemotherapy, the patients will receive intradermal injections of autologous, irradiated leukemia cells modified with DNP. After six weeks of vaccine administration, they will be skin-tested with autologous AML cells to determine whether they have developed cell-mediated immunity to their leukemia cells. Then they will be monitored to measure remission duration and survival.

Patients with AML will have achieved a complete remission after treatment with conventional chemotherapy. Patients who have relapsed after a first remission and have been induced into a second remission will also be eligible. Remission will be determined by standard CALGB criteria: absolute neutrophil count $\geq 1,500$, platelet count $\geq 100,000$, no leukemic blasts in the peripheral blood, bone marrow cellularity, >20% with maturation of all cell lines, <5% blasts in bone marrow and no Auer rods.

Patients may be excluded from the study for the following reasons: patients who are candidates for allogeneic bone marrow transplantation to support the current remission or patients who have been previously treated with allogeneic bone marrow transplantation, patients with AML of the promyelocytic type, previous exposure to other forms of immunotherapy, insufficient quantity of leukemia cells for vaccine and skin-testing (less than 100×106), Karnovsky performance status less than 80, current administration of systemic corticosteroids or cytotoxic chemotherapy, major field radiation therapy within the preceding 6 months, hematocrit<30% or total WBC<3,000, age less than 18 years, active, serious infection, concurrent active malignancy other than basal cell or squanious cell carcinoma of the skin, in situ carcinoma of the cervix, or early stage (A or B1) prostate cancer, evidence of infection with hepatitis B virus (circulating antigen) or with HIV (circulating antibody), or inability to give informed consent.

Patients with AML in initial presentation or in first relapse will be identified by their respective attending physicians. After patients have consented to blood donation, 60 ml of blood will be drawn (5 green top tubes and 1 red top tube) prior to receiving chemotherapy. Leukemic cells will be separated using a Ficoll-hypaque gradient and stored in liquid nitrogen. Then patients will be treated using standard chemotherapy protocols, including consolidation therapy, depending on the preference of their physicians. After the patients have completed their chemotherapy, they will be offered entrance onto the study. The vaccine program will be started within 8 weeks of completion of chemotherapy.

Vaccine Administration

During the first week of the study (days-7 and -5), patients will be tested for DTH response to autologous, irradiated DNP-modified leukemia cells and to PPD. On day 0 (Monday), patients will receive cyclophosphamide 300 mg/m$^2$ as a rapid IV infusion. On day 3 they will be injected intradermally with autologous leukemia vaccine; this will be repeated weekly for a total of 6 injections. Each injection will contain autologous irradiated leukemia cells modified with DNP and then mixed with BCG. The number of leukemic cells to be used with each injection will range from 2.5 to 7.5×10$^6$ cells. All vaccines will be injected into the same extremity; sites ipsilateral to a lymph node dissection will not be used. For most patients the site will be the upper dorsal arm; patients who have undergone bilateral axillary node dissection will be injected on the upper lateral thigh. Optionally, on day 0 (Monday), patients may receive cyclophosphamide 300 mg/M$^2$ as a rapid IV infusion.

Two weeks after the last vaccine, patients will undergo clinical and immunological evaluation. Patients who remain in remission will receive booster doses of vaccine at 6 and 12 months after beginning the vaccine program.

Booster Injections

Patients who have remained relapse-free will be given a seventh (booster) vaccine at the six month point. For each patient at least one cryopreserved vial of leukemia cells will be saved for the six-month booster injection. If the number of cells available is anticipated to be insufficient for 6 weekly vaccines plus the six-month booster, then the initial course of weekly injections will be reduced to 5, but no fewer. Patients who remain in remission will be given another booster vaccine at the one year point, but only if a sufficient number of cells is available. Just prior to the one-year booster, patients will be skin-tested with autologous leukemia cells to determine whether their previous level of immunity has been maintained (see 5.4).

Vaccine Preparation

Leukemia cells will be separated by centrifugation in a Ficoll-hypaque gradient. Cells in the gradient interface will be collected and washed in sterile saline. It is expected that at least 90% of these cells will be leukemia cells, the rest being circulating monocytes and lymphocytes. The cells will be aliquotted, frozen in a controlled-rate freezer and stored in liquid nitrogen until needed. On the day the patient is to be treated, the cells will be thawed, washed and irradiated. Then they will be washed again and suspended in Hanks balanced solution without phenol red.

Irradiation

In the melanoma studies (Berd et al., 1991, 1993) tumor cells used for vaccines and skin-testing were irradiated to 2500 R. That dose was more than adequate to inactivate the tumor cells so that they did not grow at vaccine or skin test sites. However, we will perform an irradiation dose-response study of leukemia cells for the first five patients to determine the minimal dose that inhibits leukemic cell proliferation. Leukemia cell suspensions will be irradiated at doses ranging from 1000 R to 10000 R. Proliferative capacity will be determined by ability to proliferate in vitro.

Modification of leukemia cells with DNP will be performed by the method of Miller and Claman. Cells are incubated for 30 minutes with DNFB under sterile conditions, followed by washing with sterile saline. The vaccine consists of 2.5 to 7.5×10$^6$ leukemia cells suspended in 0.2 ml Hanks solution. Each vaccine treatment will consist of three injections into contiguous sites.

BCG Doses

The first and second vaccines will be mixed with 0.1 ml of a 1:10 dilution of Tice BCG ("Tice-1"). The third and fourth vaccines will be mixed with 0.1 ml of a 1:100 dilution ("Tice-3"). The fifth and sixth and booster vaccines will be mixed with 0.1 ml of a 1:1000 dilution ("Tice-5"). The ideal vaccine reaction is an inflammatory papule with no more than small (<5 mm) central ulceration. If reactions are larger than this, the dose of BCG will be further attenuated. Patients who have a positive PPD (>5 mm induration) prior to receiving vaccine will have the initial dose reduced to 0.1 ml of a 1:100 dilution; subsequent doses will be determined by the previous reactions.

Immunological Evaluation

Skin testing will be performed by the intradermal injection of 0.1 ml of test material on the forearm, and delayed type hypersensitivity (DTH) will be assessed at 48 hours by measuring the mean diameter of induration. Positive reactions will be photographed. The following materials will be tested: 1) 1×10$^6$ irradiated (2500R) autologous leukemia cells unmodified and modified with DNP; 2) 3×10$^6$ irradiated (2500 R) autologous peripheral blood lymphocytes (collected at time of complete remission), unmodified and modified with DNP; 3) Hanks solution; 4) PPD-intermediate strength. Also, contact sensitivity to DNFB will be tested by applying 200 ug to the skin of the ventral surface of the upper arm and examining the area for a circle of induration at 48 hours. The full battery of DTH tests will be performed following the six week course of vaccine administration. Pre-treatment DTH testing will be limited to DNP-modified leukemia cells, PPD, and diluent. This strategy is designed to avoid: 1) sensitizing patients to DNP-modified lymphocytes and 2) tolerizing patients by injection of unmodified leukemia cells.

All patients will have blood collected for separation and cryopreservation of lymphocytes and serum each time skin testing is performed. If resources are available, these will be tested for: 1) proliferative and cytotoxic response to autologous leukemia cells; and 2) proliferative response to DNP-modified autologous lymphocytes.

Evaluation of Patients

Before beginning the vaccine program, patients will undergo a standard clinical evaluation to confirm that they are in a complete remission. CBC will be performed weekly during the period of vaccine injections. After completing the six weekly vaccine injections patients will undergo another evaluation to include CBC, SMA-12, and chest x-ray. Then the patients will be evaluated every two months for the first year, every three months for the second year and every four months for the third and subsequent years. A CBC and SMA-12 will be obtained with each visit. Bone marrow aspiration will be performed as required by abnormalities in the CBC. Duration of remission and overall survival will be measured, counting from the date of beginning the vaccine program (initial skin testing).

Pharmaceutical Information

BCG

This is the Tice strain obtained from Organon Teknika Corporation (Durham, N.C.). The freeze-dried material is reconstituted with 1 ml sterile water or phosphate buffered saline, pH 7.2 (PBS). Appropriate dilutions are made in sterile buffered saline. Then 0.1 ml is drawn up and mixed with the vaccine just before injection Cyclophosphamide This is reconstituted in sterile water and the proper dosage is administered by rapid IV infusion.

Toxicity

Cyclophosphamide

About one third of the patients in earlier melanoma vaccine protocols experienced mild nausea and vomiting after low dose cyclophosphamide. Leukopenia, alopecia, and cystitis do not occur at this dose. It is expected that this protocol will be associated with a lower incidence of nausea and vomiting than previous protocols, since cyclophosphamide will be administered only once. Nausea and vomiting will be graded according to VMO toxicity criteria.

Vaccine

All patients develop a local reaction to the BCG, consisting of a draining, tender pustule that heals in 3-4 months leaving a vaccination-like scar. As patients develop sensitivity to the BCG, the intensity of these reactions increases. Anaphylaxis, other allergic phenomena, and autoimmunity have never been observed. It is theoretically possible that injected tumor cells could grow in a patient's skin. Growth of tumor cells at vaccine or skin test sites has not been observed in more than 300 melanoma patients injected so far and is considered a very remote possibility.

Reactions at the vaccine sites will be graded as follows:

0—no symptoms

1—itching or discomfort, but no interference with arm movement or normal activity 2—discomfort causing interference with arm movement, but not requiring modification of normal activity 3—discomfort causing major interference with arm movement and requiring modification of normal activity, and 4—discomfort causing inability to use the extremity for normal activity.

DNP

A large number of patients have been sensitized to DNCB over the past 18 years (Eilber and Morton; Berd et al., 1991, 1993, 1996) without ill effects. We have injected about 300 patients with autologous melanoma cells modified with DNP by the method described above. No significant toxicities have been observed, except for the development of an urticarial eruption in a single patient, which cleared spontaneously within 5 days.

Precautions to be Taken

Patients will be observed following injection of vaccine. Patients experiencing unexpected symptoms or signs will be instructed to telephone and will be evaluated immediately. Fever that causes discomfort will be treated with acetaminophen. Nausea caused by low dose cyclophosphamide will be treated with oral prochlorperazine. If severe local reactions (ulcerations greater than 5 mm) occur at the vaccine site, subsequent doses of BCG will be reduced (see above).

Duration of the Study

Initially patients will receive only one cycle of vaccine injection (6 weekly injections). Patients without evidence of relapse will receive a booster injection at 6 and 12 months after beginning the vaccine program.

Patients who develop leukemic relapse will be considered off-study and will be treated with standard medical therapy. Also, patients will be taken off the study in the event of: 1) voluntary withdrawal or non compliance, 2) unacceptable toxicity, 3) need for administration of chemotherapy, radiation therapy, or systemic corticosteroids. All Thomas Jefferson University, NIH, and FDA regulations regarding informed consent will be followed.

Statistical Considerations

The major endpoint will be the development of DTH to DNP-modified autologous leukemia cells. In the previous studies performed in patients with malignant melanoma, 100% developed a positive DTH response ($\geq$5 mm diameter of induration) to DNP-modified autologous tumor cells following treatment, and 85% developed a large positive response ($\geq$10 mm diameter of induration). We would like to determine whether at least 50% of patients with acute leukemia develop a positive response ($\geq$5 mm diameter of induration) to DNP-modified autologous leukemic cells. Initially, we plan to treat 10 patients in first remission and 10 patients in second remission. If 9/10 in either group develop a positive response, we then can conclude with 95% confidence that the response rate of that group exceeds 50% (positive result). If fewer than 9 but more than 5 patients develop a positive response, then an additional 10 patients in that group will be studied (15/20 positives would have to be observed to be confident that the response is 50%). If less than five patients in the first remission or second remission group develop a positive response, then we will conclude that a 50% response for that group cannot be verified unless the sample size were very large (negative result).

We plan to measure remission duration and survival in these patients, although the sample size will be insufficient for statistical analysis. If a positive immunological result is obtained in either the first remission or second remission group, then an efficacy study will be developed to formally test whether DNP-vaccine prolongs relapse-free and overall survival. In addition, a phase III trial of the DNP-leukemia treatment in this patient population with a concomitant control group is planned. The required number of patients is estimated to be accrued in 2 years. This estimate is based on the number of new AML patients seen yearly at Jefferson and the potential for referral of AML from outside Jefferson.

It is expected that patients will develop DTH to DNP-modified autologous leukemia cells, and that some will develop DTH to unmodified autologous leukemia cells as well. No patients are expected to develop DTH to unmodified autologous blood lymphocytes. As a result of DNP-leukemia treatment, relapse free and total survival of these patients will be prolonged.

EXAMPLE 4

Adenocarcinoma of the Colon

Patients with resectable liver metastases constitute an ideal study system for active immunotherapy, because: 1) large amounts of tumor tissue can be obtained at the time of surgery; 2) following surgery, patients are clinically tumor-free with excellent performance status; and 3) most of these patients eventually develop recurrence and die, which underscores the need for an adjunctive therapy, such as a vaccine. Following hepatic resection, the median times to tumor recurrence and death are 11 months and 36 months, respectively.

Some evidence has accumulated that human colon carcinoma may be immunogenic and a suitable target for immunotherapy. Hoover et al. (1984, 85, 89, 93) conducted a randomized, post-surgical adjuvant study of an autologous tumor cell vaccine compared with no treatment in patients with primary, high-risk colon carcinoma. The vaccine consisted of irradiated, autologous cells derived from the primary tumor and mixed with BCG. Neither cyclophosphamide nor haptenization was employed. The vaccine did not improve survival compared to the controls. Toxicity was minimal. Schlag et al. (1992) administered vaccine to a small group of patients with colorectal cancer following resection of liver metastases. The vaccine consisted of autologous tumor cells treated with Newcastle disease virus (NDV). Nine patients exhibited increased DTH to autologous tumor cells following vaccination. After a follow-up of 18 months, 61% of the vaccinated patients had developed tumor recurrence as compared with 87% of a matched control group. No significant toxicity was observed. Fishbein et al., 1992 conducted a pilot trial of immunization with purified CEA in six patients with Dukes C and D colorectal cancer. No significant toxicity was observed, and several patients have remained tumor-free. O'Boyle et al. (1992) immunized colorectal cancer patients with modified ovine submaxillary gland mucin mixed with BCG or DETOX adjuvant. Antibody responses to a component of the immunogen were induced. Cole et al. (1996) have performed a phase I study of a vaccine consisting of recombinant Vaccinia virus expressing CEA; in vitro T cell responses to CEA were induced in some patients.

The objective is to treat patients with adenocarcinoma of the colon who have undergone resection of hepatic metastases with autologous tumor cells modified with the hapten, DNP to determine whether patients develop delayed-type hypersensitivity (DTH) to autologous carcinoma cells, and assess toxicity.

The study subjects will be patients with adenocarcinoma of the colon with liver metastases who are candidates for resection of the metastases. The surgery will be done according to standard medical practice, and the tumor tissue obtained will be sent to the laboratory for processing and cryopreservation. A small portion of the tissue will be sent to Surgical Pathology to confirm the diagnosis. After recovery from surgery, the patients will receive a six week course of treatment with a vaccine consisting of autologous, irradiated carcinoma cells modified with the hapten, dinitrophenyl (DNP). Low dose cyclophosphamide will be administered prior to the first vaccine injection. After the completion of the course of vaccine they, will be tested for delayed type hypersensitivity to autologous carcinoma cells, both DNP modified and unmodified. In vitro studies will be performed with cryopreserved lymphocytes extracted from metastatic tumors and/or separated from peripheral blood.

Patients will have adenocarcinoma of the colon or rectum with liver metastases who are candidates for surgical resection. In general, such patients will have 1-3 liver metastases that are completely resectable without evidence of other metastases. However, patients who are found to have additional, non-resectable metastases will not be excluded on that basis alone. It is anticipated that some unrespectable metastases will be treated by cryosurgery. The mass of tumor excised must be sufficient to obtain at least $100 \times 10^6$ viable tumor cells.

Patients may be excluded from this study for insufficient quantity of tumor cells for vaccine and skin-testing ($<100 \times 10^6$ cells), Karnovsky performance status less than 80, estimated survival<6 months, cytotoxic drugs taken within the preceding 8 weeks, more than two prior chemotherapies, including adjuvant chemotherapy, radiation therapy within the preceding 6 months, current administration of systemic corticosteroids, hematocrit<30% or WBC<3000, age<18, active autoimmune disease, active, serious infection, another active malignancy other than squamous cell carcinoma of skin, in situ carcinoma of the cervix, treated superficial bladder carcinoma, or early stage (A or B) prostate cancer, HIV positive by ELISA, confirmed by Western, positive for circulating hepatitis B or C antigen, or inability to give informed consent.

Surgery and Tumor Acquisition

Patients will undergo surgical resection of the hepatic metastases by standard techniques. Unrespectable metastases may be treated with cryosurgery during the initial laparotomy. Tumor tissue will be delivered to the laboratory and processed to obtain single cell suspensions. The cells will be cryopreserved and stored in liquid nitrogen.

Vaccine Administration

The vaccine program will be started at least 4 weeks after, and no more than 12 weeks after, resection of hepatic metastases. Within 4 weeks of beginning; the vaccine program, patients will undergo a clinical evaluation consisting of CBC, SMA-12, CEA. chest x-ray, and CT or MRI of the abdomen.

On day-7, patients will be skin-tested with: 1) autologous colon carcinoma cells modified with DNP (COL-DNP), 2) diluent Hanks balanced salt solution with 0.1% human albumen, and 3) PPD intermediate. DTH reactions will be measured on day 5. On day 0 (Monday), patients will receive cyclophosphamide 300 mg/$M^2$ as a rapid IV infusion. Three days later (Thursday) they will be injected intradermally with autologous colon carcinoma vaccine and this will be repeated weekly for 6 weeks. All vaccines will consist of DNP-modified, autologous colon carcinoma cells mixed with BCG. All vaccines will be injected into the left upper arm. (If for some reason a left axillary lymph node dissection had been performed, the right arm will be used.)

Two and a half weeks after the sixth vaccine, patients will undergo clinical evaluation, consisting of CBC, SMA-12, CEA, and chest x-ray. They will be tested for DTH to the following materials: autologous colon carcinoma cells, both DNP-modified and unmodified; autologous hepatocytes (obtained from original surgical specimen; autologous peripheral blood lymphocytes, both DNP-modified and unmodified; diluent; and PPD intermediate. Also, they will be tested for contact sensitivity to dinitrofluorobenzene (DNFB). A complete clinical evaluation with CT or MRI studies will be performed six months after the start of the vaccine program.

Booster Injections

Patients who have not exhibited tumor progression will be given a seventh (booster) vaccine at the six month point (measured from beginning the vaccine program). For each patient at least one cryopreserved vial of tumor cells will be saved for the six-month booster injection. If the number of cells available is anticipated to be insufficient for 6 weekly vaccines plus the six-month booster, then the initial course of weekly injections will be reduced to 5, but no fewer. Another booster vaccine will be administered one year, but only if a sufficient number of cells is available. Just prior to the one-year booster, patients will be skin-tested with autologous tumor cells to determine whether their previous level of immunity has been maintained.

Vaccine Preparation

Tumor masses will be processed as previously described (Berd et al., 1986). Cells will be extracted by enzymatic dissociation with collagenase and DNase and by mechanical dissociation, frozen in a controlled rate freezer, and stored in liquid nitrogen until needed. On the day that a patient is to be treated, the cells will be thawed, washed, and irradiated to 2500 R. Then they will be washed again and suspended in Hanks balanced salt solution without phenol red.

Modification of tumor cells with DNP will be performed by the method of Miller and Claman (1976). This involves a 30 minute incubation of tumor cells with dinitrofluorobenzene (DNFB) under sterile conditions, followed by washing with sterile saline.

The vaccine consists of a minimum of $2.5 \times 10^6$ trypan-blue-excluding tumor cells, and a maximum of $7.5 \times 10^6$ tumor cells suspended in 0.2 ml Hanks solution. Each vaccine treatment will consist of three injections into contiguous sites.

BCG Doses

The first and second vaccines will be mixed with 0.1 ml of a 1:10 dilution of Tice BCG ("Tice-1"). The third and fourth vaccines will be mixed with 0.1 ml of a 1:100 dilution ("Tice-3"). The fifth and sixth and booster vaccines will be mixed with 0.1 ml of a 1:1000 dilution ("Tice-5"). The ideal vaccine reaction is an inflammatory papule with no more than small (<5 mm) central ulceration. If reactions are larger than this, the dose of BCG will be further attenuated. Patients who have a positive PPD ($\geq 5$ mm induration) prior to receiving vaccine will have the initial dose reduced to 0.1 ml of a 1:100 dilution; subsequent doses will be determined by the previous reactions.

Skin-testing

Skift-testing will be performed by the intradermal injection of 0.1 ml of test material on the forearm, and DTH will be assessed at 48 h by measuring the mean diameter of induration. The following materials will be tested: 1) $1 \times 10^6$ irradiated autologous colon cancer cells unmodified and modified with DNP; both enzymaticallydissociated (TCE) and mechanically-dissociated (TCM) tumor cells will be used; 2) $3 \times 10^6$ autologous peripheral blood lymphocytes unmodified and modified with DNP; 3) $1 \times 10^6$ irradiated autologous hepatocytes unmodified and modified with DNP, when available from the surgical specimen; 4) Hanks solution; 5) PPD-intermediate strength. Also, contact sensitivity to DNFB will be tested by applying 200 ug to the skin of the ventral surface of the upper arm and examining the area for a circle of induration at 48 hours. The full battery of DTH tests will be performed following the six week course of vaccine administration. Pre-treatment DTH testing will be limited to DNP-modified colon cancer cells, PPD, and diluent. This strategy is designed to avoid: 1) sensitizing patients to DNP-modified lymphocytes and 2) tolerizing patients by injection of unmodified tumor cells.

All patients will have blood collected for separation and cryopreservation of lymphocytes and serum each time skin-testing is performed. Periodically, these will be tested for: response to autologous colon cancer cells. as measured by proliferation, cytokine release, and cytotoxicity.

Evaluation of Patients

Patients will be evaluated for metastatic disease before vaccine therapy is begun. After the end of the first eight weeks of vaccine therapy, evaluations will be performed every three months through year 02, every four months in year 03, and every six months thereafter. Physical examination and routine bloodwork (CBC, SMA-12, and CEA) will be performed with each evaluation. CT of the abdomen and chest x-ray will be performed prior to the administration of vaccine, at 6 months and 12 months (before vaccine boosters), and then as clinically indicated. Relapse-free and total survival will be measured. All patients will be followed for at least five years or until time of death.

Pharmaceutical Information

BCG

This is the Tice strain (substrain of the Pasteur Institute strain) obtained from Organon Teknika Corporation, Durham, N.C. The freeze-dried material is reconstituted with 1 ml sterile water or phosphate buffered saline, pH 7.2 (PBS). Appropriate dilutions are made in sterile buffered saline. Then 0.1 ml is drawn up and mixed with the vaccine just before injection.

Cyclophosphamide

This is reconstituted in sterile water and the proper dosage is administered by rapid IV infusion.

Toxicity

Cyclophosphamide

About one third of patients experience nausea and about 10% have vomiting after low dose cyclophosphamide. Leukopenia, alopecia, and cystitis do not occur at this dose. It is expected that this protocol will be associated with a lower incidence of nausea and vomiting than previous protocols, since cyclophosphamide will be administered only once.

Vaccine

All patients develop a local reaction to BCG, consisting of a draining, tender pustule that heals in 2-3 months leaving a smallpox vaccination-like scar. As patients develop sensitivity to BCG, the intensity of these reactions increases. Anaphylaxis, other allergic phenomena, and auto-immunity have never been observed. It is theoretically possible that injected tumor cells could grow in a patient's skin. However, this has not been observed in more than 200 patients injected so far and is considered a very remote possibility.

Reactions at the vaccine sites will be graded as follows:
0—no symptoms
1—itching or discomfort, but no interference with arm movement or normal activity
2—discomfort causing interference with arm movement, but not requiring modification of normal activity
3—discomfort causing major interference with arm movement and requiring modification of normal activity, and
4—discomfort causing inability to use the extremity for normal activity.

DNP

As noted above, a large number of patients have been sensitized to DNCB over the past 18 years (Eilber and Morton; Berd et al., 1982, 1984) without ill effects. We have injected about 200 patients with autologous melanoma cells modified with DNP by the method described above. No significant toxicities have been observed, except for the development of an urticarial eruption in a single patient, which cleared spontaneously within 5 days.

Precautions to be Taken

Patients will be observed following injection of vaccine. Patients experiencing unexpected symptoms or signs will be instructed to telephone and will be evaluated immediately. Fever that causes discomfort will be treated with acetaminophen. Nausea caused by low dose cyclophosphamide will be treated with oral prochlorperazine (Compazine). If severe local reactions (>5 mm ulceration) occur at the vaccine site, subsequent doses of BCG will be reduced (see above).

Duration of Study

1) Patients who are relapse-free at the 1 year evaluation will receive a final booster injection of vaccine. Then they will be followed without further treatment.
2) Patients who develop progressive metastases will be taken off study and treated as clinically indicated (usually chemotherapy). All Thomas Jefferson University, NIH, and FDA regulations regarding informed consent will be followed.

Statistical Considerations

The major endpoint will be the development of DTH to DNP-modified autologous tumor cells. In our studies of DNP-modified autologous vaccine for melanoma, 100% of patients (N=60) developed a positive DTH response ($\geq 5$ mm diameter of induration) to DNP-modified autologous tumor cells following treatment, and 85% developed a large positive response ($\geq 10$ mm diameter of induration). We would like to determine whether at least 50% of colon carcinoma patients develop a positive response ($\geq 5$ mm) to DNP-modified autologous colon carcinoma cells. Initially, we plan to treat 10 patients. If 9 develop a positive response, then we can conclude with 95% confidence that the response rate exceeds 50%, and the study will be terminated ("positive" result). If <9 but $\geq 5$ patients develop a positive response, then an additional 10 patients will be studied. (15/20 positives would have to be observed to be confident that the response is 50%.) If <5 patients develop a positive response, then we will conclude that a 50% response rate cannot be verified unless the sample size is very large ("negative" result).

If a "positive" result is obtained, we will perform an efficacy study to determine whether DNP-vaccine prolongs relapse-free and/or total survival in these patients. In addition, a phase III trial of the DNP-colon cancer treatment in this patient population with a concomitant control group is planned. Subsequently, clinical studies may be performed in patients with non-metastatic colon adenocarcinoma, e.g., primary colon carcinoma that has a high risk of recurring. We will measure survival parameters in the current study (Kaplan-Meier method). A striking improvement in two-year relapse-free survival-would be highly encouraging, but the sample size will be too small to allow for formal statistical analysis. Since Thomas Jefferson University Hospital performs hepatic resection on about 30 stage IV colon carcinoma patients yearly, we expect that accrual of patients will be completed in less than one year.

It is expected that patients will develop DTH to DNP-modified autologous colon carcinoma cells, and that some will develop DTH to unmodified autologous colon carcinoma cells as well. No patients are expected to develop DTH to unmodified autologous blood lymphocytes. As a result of DNP-colon cell treatment, relapse free and total survival of these patients will be prolonged.

Various modifications of the invention in addition to those shown and described herein will be apparent to those skilled in the art from the foregoing description. Such modifications are also intended to fall within the scope of the appended claims.

The disclosures of each patent, patent application and publication cited or described in this document are hereby incorporated herein by reference, in their entirety.

EXAMPLE 5

Ovarian Carcinoma

The objectives of this study was to treat ovarian cancer patients by administering autologous tumor cells modified with DNP. At the time of the treatment, nine patients (that have undergone surgery and chemotherapy) did not have any evidence of tumor. The study was undertaken to measure the delayed-type hypersensitivity (DTH) to autologous cancer cells and to assess toxicity.

Each patient was initially treated according to standard medical practice (debulking surgery followed by chemotherapy). Patients who underwent either optimal or suboptimal debulking were eligible for the study. The mass of tumor excised from each patient was sufficient to obtain at least $100 \times 10^6$ viable tumor cells.

The patients received chemotherapy and were clinically tumor-free following completion of chemotherapy (i.e., normal physical examination and CT studies and serum CA-125<35 IU/L). Within 12 weeks after surgery, all patients began chemotherapy with carboplatin or cisplatin+taxol according to standard medical practice. Six cycles of chemotherapy were administered.

Between 4 and 12 weeks after completion of chemotherapy, patients underwent a metastatic evaluation including computerized tomography (CT) of chest-abdomen-pelvis. Only patients with no evidence of recurrent carcinoma were eligible for vaccine treatment. Patients with elevated serum level of CA125 were eligible providing that CT studies were negative for recurrence.

Each patient received six weekly vaccine injections consisting of autologous, irradiated ovarian carcinoma cells modified with dinitrophenyl (DNP). Low dose cyclophosphamide (300 mg/M$^2$) was be administered prior to the first vaccine injection. The vaccination dose contained from about 2.5 to about 7.5×10$^6$ trypan-blue-excluding tumor cells suspended in 0.2 ml Hanks solution with human serum albumin. The cells were prepared and conjugated to the hapten as described in Example 1.

On day-7, patients were skin-tested with: 1) autologous ovarian carcinoma cells modified with DNP (OV-DNP), 2) diluent (Hanks balanced salt solution with 0.1% human serum albumin, and 3) PPD intermediate. DTH reactions were measured on day-5. On day 0, patients received cyclophosphamide 300 mg/M$^2$ as a rapid IV infusion. Three days later the patients were injected intradermally with autologous ovarian carcinoma vaccine and this was repeated weekly for 6 weeks. Vaccines consisted of DNP-modified, autologous ovarian carcinoma cells mixed with BCG. The first and second vaccines were mixed with 0.1 ml of a 1:10 dilution of Tice BCG ("Tice-1"). The third and fourth vaccines were mixed with 0.1 ml of a 1:100 dilution ("Tice-3"). The fifth and sixth and booster vaccines were mixed with 0.1 ml of a 1:1000 dilution ("Tice-5"). Vaccines were injected into the upper arm.

After the completion of the vaccine treatment the patients were tested for delayed type hypersensitivity to autologous carcinoma cells, both DNP-modified and unmodified as described in Example 1. They were tested for DTH to the following materials: autologous ovarian carcinoma cells, both DNP-modified and unmodified; autologous peripheral blood lymphocytes, both DNP-modified and unmodified; diluent; and PPD intermediate. Also, they were tested for contact sensitivity to dinitrofluorobenzene (DNFB). Two and a half weeks after the sixth vaccine, patients underwent clinical evaluation, such as CBC, SMA-12, CA125, and chest x-ray. All patient evaluation and follow-up will be as described in Example 1.

Patients who remained relapse-free received a seventh (booster) vaccine at the six month point (measured from the beginning of the vaccine program). For each patient at least one cryopreserved vial of tumor cells was saved for the six-month booster injection. Another booster vaccine will be administered at the twelve month point, but only if a sufficient number of cells is available. Just prior to the one-year booster, the patients will be skin-tested with autologous tumor cells to determine whether their previous level of immunity has been maintained. Relapse-free and total survival are being measured. All patients will be followed for at least five years or until the time of death.

Results

Nine patients have been entered onto the study and results are available for each patient. No serious toxicity was observed. Delayed-Type Hypersensitivity (DTH) Results (Mm induration) are reported in the following Table.

| Patient | Date Applied | DNP-TCM | DNP-TCE | unmod TCE | unmod TCM | Lymphs | DNP-Lymphs | Enzyme-Lymphs | DNFB | Diluent | PPD |
|---|---|---|---|---|---|---|---|---|---|---|---|
| OV-1 | Jan. 20, 1997 | 2 | | | | | | | | | 0 |
| OV-1 | Mar. 24, 1997 | 20 | 14 | 7 | 8 | 0 | 3 | 0 | 0 | | 27 |
| OV-11 | Jan. 13, 1997 | | 17 | | | | | | | | |
| OV-11 | Jan. 13, 1997 | 17 | 14 | | 0 | 2 | 3 | 2 | 2 | 0 | 28 |
| OV-11 | Nov. 12, 1997 | 3 | | | | | | | | 0 | 2 |
| OV-13 | Feb. 16, 1998 | 2 | | | | | | | | 0 | 0 |
| OV-13 | Apr. 21, 1998 | 6 | 7 | 0 | 5 | 0 | 0 | 0 | 1 | 0 | 19 |
| OV-15 | Apr. 27, 1998 | 0 | | | | | | | | 0 | 0 |
| OV-15 | Jul. 7, 1998 | 6 | 4 | 5 | 5 | 0 | 0 | 0 | | 0 | 23 |
| OV-15 | Jul. 9, 1998 | | | | | | | | 1 | | |
| OV-2 | Jan. 28, 1997 | 4 | | | | | | | | | 0 |
| OV-2 | Mar. 31, 1997 | 28 | 25 | 7 | 8 | 0 | 8 | 0 | 2 | | 28 |
| OV-3 | Apr. 1, 1997 | 0 | | | | | | | | | 0 |
| OV-3 | Jun. 2, 1997 | 5 | 7 | 7 | 8 | 0 | 3 | 3 | 1 | | 22 |
| OV-3 | Jun. 2, 1997 | 7 | | | 7 | | | | | | |
| OV-4 | May 6, 1997 | 0 | | | | | | | | | 0 |
| OV-4 | Jul. 7, 1997 | 13 | 17 | 5 | 5 | 0 | 8 | 0 | 1 | | 34 |
| OV-4 | May 19, 1998 | 10 | 13 | 5 | 6 | 0 | 7 | | | 0 | |
| OV-5 | May 21, 1997 | 10 | | | | | | | | | 5 |
| OV-5 | Jul. 22, 1997 | 14 | 10 | 7 | 15 | 0 | 0 | 0 | 1 | | 25 |
| OV-5 | Jul. 22, 1997 | 15 | | | 4 | | | | | | |
| OV-6 | May 20, 1997 | 11 | | | | | | | | | 0 |
| OV-6 | Jul. 21, 1997 | 17 | 15 | 11 | 17 | 0 | 0 | 0 | 0 | | 0 |
| OV-6 | May 19, 1998 | 10 | 10 | 8 | 8 | 0 | 0 | | | 0 | |

Thus, following administration of DNP-modified autologous ovarian carcinoma vaccine, 9 out of 9 patients developed DTH to DNP-modified and 8 out of 9 to unmodified autologous ovarian carcinoma cells. From the statistics point of view, this study is now complete and indicates that the response rate is at least 50%. One patient has died since and 8 patient remain in the follow-up study.

EXAMPLE 6

Advanced Ovarian Carcinoma

The objectives of this study was to treat ovarian cancer in patients with measurable disease at the time of the vaccine treatment. Nine patients have undergone surgery and chemotherapy as described in Example 5. The study was undertaken to measure the delayed-type hypersensitivity (DTH) to autologous cancer cells and to assess toxicity.

The treatment and evaluations were conducted and the vaccines and the reagents were prepared as described in Example 5.

Results

Nine patients have been entered onto the study and seven were evaluable. No serious toxicity has been observed. Delayed-Type Hypersensitivity (DTH) Results (Mm induration) are reported in the following Table.

| Patient | Date Applied | DNP-TCM | DNP-TCE | unmod TCE | unmod TCM | Lymphs | DNP-Lymphs | Enzyme-Lymphs | DNFB | Diluent | PPD |
|---|---|---|---|---|---|---|---|---|---|---|---|
| OV-10 | Sep. 16, 1997 | 3 | | | | | | | | 0 | 0 |
| OV-10 | Nov. 18, 1997 | 2 | | | 6 | 0 | 0 | 0 | 1 | 0 | 24 |
| OV-12 | Jan. 20, 1998 | 0 | | | | | | | | 0 | 0 |
| OV-12 | Mar. 23, 1998 | 16 | | | 0 | | | | | | |
| OV-12 | Mar. 23, 1998 | 20 | | | 4 | 0 | 13 | 0 | | 0 | 22 |
| OV-14 | Apr. 28, 1998 | 16 | | | | | | | | 0 | 0 |
| OV-14 | Jun. 29, 1998 | 8 | 7 | 7 | 5 | 0 | 0 | 0 | 1 | 0 | 10 |
| OV-16 | May 18, 1998 | 2 | | | | | | | | 0 | 0 |
| OV-16 | Jul. 20, 1998 | 7 | | | 8 | 0 | 0 | 3 | 0 | 0 | 22 |
| OV-17 | May 20, 1998 | 2 | | | | | | | | 0 | 2 |
| OV-17 | Jul. 21, 1998 | 26 | 25 | 5 | 6 | 0 | 8 | 0 | | 0 | 17 |
| OV-18 | Jun. 30, 1998 | 0 | | | | | | | | 0 | 0 |
| OV-7 | Jun. 17, 1997 | 0 | | | | | | | | 0 | |
| OV-8 | Jul. 9, 1997 | 0 | | | | | | | | | 0 |
| OV-8 | Sep. 17, 1997 | 0 | | | 0 | 0 | 0 | 5 | 0 | 0 | 0 |
| OV-9 | Aug. 25, 1997 | | 0 | | | | | | | 0 | 0 |
| OV-9 | Oct. 28, 1997 | | 10 | 5 | | 0 | 3 | 0 | 0 | 0 | 21 |

Thus, following administration of DNP-modified autologous ovarian carcinoma vaccine, 5 out of 7 patients developed DTH to DNP-modified and 5 out of 7 to unmodified autologous ovarian carcinoma cells. Two patients have died since and five patients remain in the follow-up study.

REFERENCES

Andreasen, R. B., Biberfeld, P., Ost, A., Reizenstein, P., and Olsson, L. Specificity and diagnostic implications of the reactivity pattern of a panel of monoclonal antibodies against myeloid leukemia cells. *Scand. J. Haematol.* 37:323-332, 1986.

Ashman, L. K., Kriek, G. W., Cooper, S. J., and O'Keefe, D. E. Requirements for the stimulation of allogeneic T lymphocytes by acute non-lymphoblastic leukaemia cells. *Cancer Immunol. Immunother.* 25:250-256, 1987.

Berd D, H. C. Maguire, Jr., E. Hart, and M. J. Mastrangelo: Post-surgical adjuvant therapy of melanoma with a dinitrophenyl (DNP)-modified vaccine: prolongation of disease-free and total survival. *Proc. Amer. Assoc. Clin. Oncol.*, 12:A1319, 1993.

Berd D, Maguire H C Jr, and Mastrangelo M J: Induction of cell-mediated immunity to autologous melanoma cells and regression of metastases after treatment with a melanoma cell vaccine preceded by cyclophosphamide. *Cancer Res.*, 46:2572-2577, 1986.

Berd D, Murphy G, Maguire H C Jr, Mastrangelo M J: Immunization With—Haptenized, Autologous Tumor Cells Induces Inflammation of Human Melanoma Metastases. *Cancer Res,* 51:2731-2734, 1991

Berd, D., Maguire, H. C., Jr., and Mastrangelo, M. J. Treatment of human melanoma with a hapten-modified autologous vaccine. *Ann. NY. Acad. Sci.* 690:147-152, 1993.

Berd, D., Maguire, H. C., Nathan, F. N., Schuchter, L. M., Bloome, E., and Mastrangelo, M. J. Autologous, DNP-modified vaccine as post-surgical adjuvant treatment of stages III and IV melanoma. *Proc. Am. Soc. Clin. Oncol.* 15:#1805: 5541996.(Abstract)

Berd, D., Mastrangelo, M. J., Engstrom, P. F., Paul, A., and Maguire, H. Augmentation of the human immune response by cyclophosphamide. *Cancer Res.* 42:4862-4866, 1982.

Boon T, Cerottini J C, Van den Eynde B, van der Bruggen P, Van Pel A. Tumor antigens recognized by T lymphocytes. *Annu Rev Immunol* 1994; 12:337-365

Bowen-Yacyshyn, M. B., Poppema, S., Berg, A., MacLean, G. D., Reddish, M. A., Meikle, A., and Longenecker, B. M. CD691 and HLA-DRI activation antigens on peripheral blood lymphocyte populations in metastatic breast and ovarian-cancer patients: Correlations with survival following active specific immunotherapy. *Int. J. Cancer,* 61:470-474, 1995.

Caron P C, Scheinberg D A. Immunotherapy for acute leukemias. *Current opinion in Oncology.* 1994:6:14-22

Cohen, P. J., Lotze, M. T., Roberts, J. R., Rosenberg, S. A., and Jaffe, E. S. The immunopathology of sequential tumor biopsies in patients treated with interleukin-2. Correlation of response with T-cell infiltration and HLA-DR expression. *Am. J. Pathol.* 129:208-216, 1987.

Cole, D. J., Wilson, M. C., Baron, P. L., O'Brien, P., Reed, C., Tsang, K. Y., and Schlom, J. Phase I study of recombinant CEA vacciiiia virus vaccine with post vaccination CEA peptide challenge. *Hum. Gene Ther.* 7:1381-1394, 1996.

Eilber, F. R. and Morton, D. L.: Impaired immunologic reactivity and recurrence following cancer surgery. *Cancer* 25:362-367, 1970.

Elder, D. E., Ainsworth, A. M., and Clark, W. H., Jr. The surgical pathology of cutaneous malignant melanoma. In: W. H. Clark, Jr., L. I. Goldman and M. J. Mastrangelo (eds.), Human malignant melanoma, pp. 55-108,New York: Grune and Stratton. 1979.

Ferrini, S., Biassoni, R., Moretta, A., Bruzzone, M., Nicolin, A., and Moretta, L. Clonal analysis of T lymphocytes isolated from ovarian carcinoma ascitic fluid. Phenotype and functional characterization of T-cell clones capable of lysing autologous carcinoma cells. *Int. J. Cancer,* 36:337-344, 1985.

Fishbein, G. E., McClay, E., Berd, D., and Mastrangelo, M. J. A post surgical adjuvant trial of CEA immunization in patients with Dukes C and D colorectal cancer: A pilot study. *Vaccine Res.* 1:123-128, 1992.

Flood, P. M., Schreiber, H., and Ron, Y.: Protective immunity to progressive tumors can be- induced by antigen presented regressor tumors. *J. Immunol.* 138:3573-3579, 1987.

Foon K A, Smalley R V, Riggs C W, Gale R P. The role of immunotherapy in acute myelogenous leukemia. *Arch Intern Med* 1983; 143:1726-1731

Fujiwara, H., Aoki, H., Yoshioka, T., Tomita, S., Ikegami, R., and Hamaoka, T. Establishment of a tumor-specific immunotherapy model utilizing TNP-reactive helper cell activity and its application to the autochthonous tumor system. *J. Immunol.* 133:509-514, 1984.

Fujiwara, H., Aoki, H., Yoshioka, T., Tomita, S., Ikegami, R., and Hamaoka, T.: Establishment of a tumor-specific immunotherapy model utilizing TNP-reactive helper cell activity and its application to the autochthonous tumor system. *J. Immunol.,* 133:509-514, 1984.

Gale R P, Champlin R E. How does bone-marrow transplantation cure leukemia? *The Lancet.* 1984.

Galili, N., Naor, D., Asjo, B., and Klein, G. Induction of immune responsiveness in a genetically low-responsive tumor-host combination by chemical modification of the immunogen. *Eur. J. Immunol.* 6:473-476, 1976.

Greiner, J. W., Guadagni, F., Goldstein, D., Smalley, RN., Borden, E. C., Simpson, J. F., Molinolo, A., and Schlom, J. Intraperitoneal administration of interferon-gamma to carcinoma patients enhances expression of tumor-associated glycoprotein-72 and carcinoembryonic antigen on malignant ascites cells. *J. Clin. Oncol.* 10:735-746, 1992.

Hoover, H. C., Jr. and Hanna, M. G., Jr. Active immunotherapy in colorectal cancer. *Sem. Surg. Oncol.* 5:436-440, 1989.

Hoover, H. C., Jr., Brand . horst, J. S., Peters, L. C., Surdyke, M. G., Takeshita, Y., Madariaga, J., Muenz, L. R., and Hanna, M. G., Jr. Adjuvant active specific immunotherapy for human colorectal cancer: 6.5-year median follow-up of a phase III prospectively randomized trial. *J. Clin. Oncol.* 11:390-399, 1993.

Hoover, H. C., Jr., Surdyke, M., Dangel, R. B., Peters, L. C., and Hanna, M. G., Jr. Delayed cutaneous hypersensitivity to autologous; tumor cells in colorectal cancer patients immunized with an autologous tumor.cell:bacillus Calmette-Guerin vaccine. *Cancer Res.* 44:1671-1676, 1984.

Hoover, H. C., Jr., Surdyke, M. G., Dangel, R. B., Peters, L. C., and Hanna, M. G., Jr. Prospectively randomized trial of adjuvant active-specific immunotherapy for human colorectal cancer. *Cancer,* 55:1236-1243, 1985.

Horowitz M, Gale R P, Sondel P M et al. Graft-versus-Leukemia reactions after bone marrow transplantation. *Blood* 1990;75:555-562.

Ioannides, C. G., Freedman, R. S., Platsoucas, C. D., Rashed, S., and Kim, Y. P. Cytotoxic T cell clones isolated from ovarian tumor-infiltrating lymphocytes recognize multiple antigenic, epitopes on autologous tumor cells. *J. Immunol.* 146:1700-1707, 1991.

Keating M J, Estey E, Kantarjian H. Acute Leukemia. In: DeVita VT, Hellman S, Rosenberg S A, eds. Cancer: Principles and Practice of Oncology.4th ed. Philadelphia: Lippincott 1993: 1938-1964.

Kim, B. S. and Jang, Y. S., Constraints in antigen processing result in unresponsiveness to a T cell epitope of hen egg lysozyme in C57BL/6 mice. *Eur. J. Immunol.* 22, 775782, 1992.

Laucius, J. F., Bodurtha, A. J., Mastrangelo, M. J., and Bellet, R. E. A Phase II study of autologous irradiated tumor cells plus BCG in patients with metastatic malignant melanoma. *Cancer,* 40:2091-2093, 1977.

McCune, C. S., Schapira, D. V., and Henshaw, E. C. Specific immunotherapy of advanced renal carcinoma: evidence for the polyclonality of metastases. *Cancer,* 47:1984-1987, 1981.

Maclean, G., Bowen-Yacyshy, M. B., Samuel, J., Meikle, A., Stuart, G., Nation, J., Poppema, S., Jerry, M., Koganty, R., Wong, T., and Longenecker, B. M. Active immunization of human ovarian cancer patients against a cominon carcinoma (Thomsen-Friedenreich) determinant using a synthetic carbohydrate antigen. *J. Immunother.* 11:292-305, 1992.

Mallmann, P. Autologous tumor-cell vaccination and lymphokine-activated tumorinfiltrating lymphocytes (LAK-TIL). *Hybridoina,* 12:559-566, 1993.

Martin, S., Von Bonin, A., Fessler, C., Pflugfelder, U., and Weltzien, H. U., Structural complexity of antigenic determinants for class I MHC-restricted, haptenspecific T cells: Two qualitatively differing types of H-2 Kb-restricted TNP epitopes. *J. Immunol.* 151:678-687, 1993.

Miller, S. D. and Claman, H. N.: The induction of hapten-specific T cell tolerance by using hapten-modified lymphoid cells. I.Characteristics of tolerance induction. *J. Immunol.* 117:1519-1526, 1976.

Mitchell, M. S., Harel, W., Kempf, R. A., Hu, E., Kan-Mitchell, J., Boswell, W. D., Dean, G., and Stevenson, L. Active-specific immunotherapy for melanoma. *J. Clin. Oncol.* 8:856-869, 1990.

Mobus, V., Horn, S., Stock, M., and Schirrmacher, V. Tumor cell vaccination for gynecological tumors. *Hybridoma,* 12:543-547, 1993.

Morton, D. L., Nizze, A., Famatiga, E., Hoon, D. S. B., Gupta, R., and Irie, R. Clinical results of a trial of active specific immunotherapy with melanoma cell vaccine and immunomodulation in metastatic melanoma. *Proc. Am. Assoc. Cancer Res.* 30:1520:1989. (Abstract)

O'Boyle, K. P., Zamore, R., Adluri, S., Cohen, A., Kemeny, N., Welt, S., Lloyd, K. O., Oettgen, H. F., Old, L. J., and Livingston, P. O. Immunization of colorectal cancer patients with modified ovine submaxillary gland mucin and adjuvants induces IgM and IgG antibodies to sialylated Tn. *Cancer Res.* 52:5663-5667, 1992.

Ortinann, B., Martin, S., Von Bonin, A., Schiltz, E., Hoschiitzky, H., and Weltzien, H. U., Synthetic peptides anchor T cell-specific TNP epitopes to MHC antigens. *J. Immunol.* 148:1445-1450, 1992.

Powles, R. Immunotherapy for acute myelogenous leukemia using irradiated and unirradiated leukemia cells. *Cancer,* 34:suppl: 1558-62, 1974.

Powles, R. L., Russell, J. A., Selby, P. J., Prentice, H. G., Jones, D. R., McElwain, T. J., and Alexander, P. Maintenance of remission in acute myelogenous leukaemia by a mixture of B.C.G. and irradiated leukaemia cells. *Lancet,* 2:1107-1110, 1977.

Sato, T., Maguire, H. C., Jr., Mastrangelo, M. J., and Berd, D. Human immune response to DNP-modified autologous cells after treatment with a DNP-conjugated melanoma vaccine. *Clin. Immunol. Immunopathol.* 74:35-43, 1995. (Abstract)

Schlag, P., Manasterski, M., Gerneth, T., Holienberger, P., Dueck, M., Herfarth, C., Liebrich, W., and Schirrmacher, V. Active specific immunotherapy with Newcastle disease-virus-modified autologous tumor cells following resection of liver metastases in colorectal cancer. First evaluation of clinical response of a phase II-trial. *Cancer Immunol. Immunother.* 35:325-330, 1992.

Shearer, G. M. Cell-mediated cytotoxicity to trinitrophenyl-modified syngeneic lymphocytes. *Eur. J. Immunol.* 4:527-533, 1974.

Vaccarello, L., Wang, Y. L., and Whiteside, T. L. Sustained outgrowth of autotumorreactive T lymphocytes from human ovarian carcinomas in the presence of tumor necrosis factor a and interleukin 2. *Hum. Immunol.* 28:216-227, 1990.

Yamada, A., Kataoka, A., Shichijo, S., Kaniura, T., Imai, Y., Nishida, T., and Itoh, K. Expression of -MAGE-1, MAGE-2, MAGE-31-6 and MAGE-4al-4b genes in ovarian tumors. *Int. J. Cancer,* 64:388-393, 1995.

What is claimed is:

1. A method of treating colon carcinoma consisting of administering a single dose of cyclophosphamide to a human, followed by at least six weekly administrations of a composition comprising a therapeutically effective amount of a hapten modified, irradiated autologous colon carcinoma cell and an adjuvant, wherein said adjuvant is Bacille Calmette-Guerin, and further followed by administration of at least one booster composition comprising an amount of a hapten modified, irradiated autologous colon carcinoma cell and an adjuvant, wherein said adjuvant of said booster composition is Bacille Calmette-Guerin.

2. The method of claim 1, wherein said hapten is dinitrophenyl.

3. The method of claim 1, said method further comprising eliciting T lymphocytes infiltrating said colon carcinoma.

* * * * *